(12) United States Patent
Melucci et al.

(10) Patent No.: US 9,761,810 B2
(45) Date of Patent: Sep. 12, 2017

(54) ORGANIC SEMICONDUCTOR MATERIAL

(71) Applicant: E.T.C. S.r.l., Bologna (IT)

(72) Inventors: Manuela Melucci, Bologna (IT); Laura Favaretto, Ozzano Nell'Emilia (IT); Massimo Zambianchi, Cesena (IT); Raffaella Capelli, Bologna (IT); Michele Muccini, Bologna (IT)

(73) Assignee: E.T.C. S.R.L., Lainate (MI) (IT)

( * ) Notice: Subject to any disclaimer, the term of this patent is extended or adjusted under 35 U.S.C. 154(b) by 0 days.

(21) Appl. No.: 14/570,777

(22) Filed: Dec. 15, 2014

(65) Prior Publication Data

US 2015/0311448 A1    Oct. 29, 2015

Related U.S. Application Data

(63) Continuation of application No. 14/114,892, filed as application No. PCT/IB2012/052503 on May 18, 2012, now abandoned.

(30) Foreign Application Priority Data

May 18, 2011 (IT) .................. 12011A0881

(51) Int. Cl.

| | | |
|---|---|---|
| *H01L 51/00* | (2006.01) | |
| *C07D 495/04* | (2006.01) | |
| *C07D 495/14* | (2006.01) | |
| *C07D 495/22* | (2006.01) | |
| *C07D 519/00* | (2006.01) | |
| *H01L 51/05* | (2006.01) | |
| *H01L 51/10* | (2006.01) | |

(52) U.S. Cl.
CPC ........ *H01L 51/0068* (2013.01); *C07D 495/04* (2013.01); *C07D 495/14* (2013.01); *C07D 495/22* (2013.01); *C07D 519/00* (2013.01); *H01L 51/0071* (2013.01); *H01L 51/001* (2013.01); *H01L 51/0053* (2013.01); *H01L 51/052* (2013.01); *H01L 51/0512* (2013.01); *H01L 51/0545* (2013.01); *H01L 51/105* (2013.01); *H01L 2251/308* (2013.01)

(58) Field of Classification Search
None
See application file for complete search history.

(56) References Cited

U.S. PATENT DOCUMENTS

| | | |
|---|---|---|
| 5,276,009 A | 1/1994 | Muenster et al. |
| 2015/0214488 A1 | 7/2015 | Melucci et al. |
| 2015/0287932 A1 | 10/2015 | Zambianchi et al. |
| 2015/0311448 A1 | 10/2015 | Melucci et al. |

FOREIGN PATENT DOCUMENTS

| | | |
|---|---|---|
| DE | 1954550 | 7/1971 |
| EP | 0467206 | 1/1992 |
| JP | 2009099942 A | 5/2009 |
| WO | 2006/094292 | 9/2006 |
| WO | 2008/127029 | 10/2008 |
| WO | 2010/131764 A1 | 11/2010 |

OTHER PUBLICATIONS

PCT International Search Report dated Jul. 5, 2012 for PCT Application PCT/IB2012/052503 filed on May 18, 2012 in the name of E.T.C. S.R.L.
PCT Written Opinion dated Jul. 5, 2012 for PCT Application PCT/IB2012/052503 filed on May 18, 2012 in the name of E.T.C. S.R.L.
PCT International Preliminary Report on Patentability dated May 24, 2013 for PCT Application PCT/IB2012/052503 filed on May 24, 2014 in the name of E.T.C. S.R.L.
Hong, W., et al. *Linera Fused Dithieno [2, 3-b:3'2'-d]-thiopene Diimides*. Organic Letters, vol. 13 (6), pp. 1410-1413. Mar. 18, 2011.
Gaina, C. et al. *Polyimides containing 1,4-dithiine units and their corresponding thiophene 2,3,4,5 tetracarboxylimide units*. High Performance Polymers, Institute of Physics Publishing, Bristol, GB, vol. 11(2), pp. 185-195. Jun. 1, 1999.
Ronova, I. et al. *The effect of the conformational rigidity on the initial decomposition temperature of some heterocyclic polyimides*. High Performance Polymers, Institute of Physics Publishing, Bristol, GB, vol. 14(2), pp. 197-202. Jan. 1, 2002.
Sonar, P. et al., "A Low-Bandgap Diketopyrrolopyrrole-Benzothiadiazole-Based Copolymer for High-Mobility Ambipolar Organic Thin-Film Transistors" Adv. Mater. 2010, 22, 5409-5413.
Facchetti, A. et al., "Building Blocks for N-Type Organic Electronics: Regiochemically Modulated Inversion of Majority Carrier Sign in Perfluoroarene-Modified Polythiophene Semiconductors" Angew. Chem. Int. Ed. 2003, 42, 3900-3903.
Zhang, Q.T. et al., "Alternating Donor/Acceptor Repeat Units in Polythiophenes. Intramolecular Charge Transfer for Reducing Band Gaps in Fully Substituted Conjugated Polymers" J. Am. Chem. Soc. vol. 120, No. 22, 1998.
Pomerantz, M., "Planar 2,2'-bithiophenes with 3,3'- and 3,3',4,4'-substituents. A computational study" Tetrahedron Letters 44, 2003, 1563-1565.
Nielsen, C.B., "New Regiosymmetrical Dioxopyrrolo- and Dihydropyrrolo-Functionalized Polythiophenes" Org. Lett. vol. 6, No. 19, 2004.
Yoon, M-H., "Organic Thin-Film Transistors Based on Carbonyl-Functionalized Quarterhiophenes: High Mobility N-Channel Semiconductors and Ambipolar Transport" J. Am. Chem. Soc. 2005, 127, 1348-1349.
Bijleveld, J.C., "Poly(diketopyrrolopyrrole-terthiophene) for Ambipolar Logic and Photovoltaics" J. Am. Chem. Soc. 2009, 131, 16616-16617.
Melucci et al, "Polyvinyl-Locked versus Free Quaterthiophene: Effect of Spacital Contraints on the Electronic Properties of n-Hexylquaterthiophene" Chem.Phys.Chem. 2007, 8, 2621-2626.

(Continued)

*Primary Examiner* — Alicia L Otton
(74) *Attorney, Agent, or Firm* — Steinfl + Bruno LLP

(57) ABSTRACT

Novel compounds useful as organic semiconductor material are described. Semiconductor devices containing said organic semiconductor material are also described.

14 Claims, 10 Drawing Sheets

(56) References Cited

OTHER PUBLICATIONS

A. Facchetti, M. Mushrush, H.E. Katz, T.J. Marks "n-Type Buliding Blocks for Organic Electronics: A Homologous Family of Fourocarbon-Substitute Thiophene Oligomers with High Carrier Mobility" *Adv. Mat.* 15 (2003) 35-38.
Letizia, J.A. et al., "n-Channel Polymers by Design: Optimizing the Interplay of Solubilizing Substituents, Crystal Packing, and Field-Effect Transistor Characteristics in Polymeric Bithiophene-Imide Semiconductors" *J. Am. Chem. Soc.* 2008, 130, 9679-9694.
Muccini, M. "A bright future for organic field-effect transistors", Nature Materials, vol. 5, No. 8, 1 (2006), pp. 605-613.
Restriction Requirement for U.S. Appl. No. 14/423,074, filed Feb. 20, 2015 on behalf of Manuela Melucci. dated: Apr. 22, 2016. 9 pages.
International Search Report for PCT Application No. PCT/IB2013/059200 filed Oct. 8, 2013 on behalf of E.T.C. S.R.L. dated: Dec. 13, 2013. 3 pages.
Written Opinion for PCT Application No. PCT/IB2013/059200 filed Oct. 8, 2013 on behalf of E.T.C. S.R.L. dated: Dec. 13, 2013. 4 pages.
Non-Final Office Action for U.S. Appl. No. 14/435,411, filed Apr. 13, 2015 on behalf of Manuela Melucci. dated: Jan. 13, 2016. 34 pages.
Final Office Action for U.S. Appl. No. 14/435,411, filed Apr. 13, 2015 on behalf of Manuela Melucci. dated: Jun. 24, 2016. 12 pages.
International Search Report for PCT Application No. PCT/IB2013/060128 filed Nov. 14, 2013 on behalf of E.T.C. S.R.L. dated: Jan. 7, 2014. 4 pages.
Written Opinion of the International Searching Authority for PCT Application No. PCT/IB2013/060128 filed Nov. 14, 2013 on behalf of E.T.C. S.R.L. dated: Jan. 7, 2014. 6 pages.
Written Opinion of the International Preliminary Examining Authority for PCT Application No. PCT/IB2013/060128 filed Nov. 14, 2013 on behalf of E.T.C. S.R.L. dated: Nov. 3, 2014. 6 pages.
International Preliminary Report on Patentability for PCT Application No. PCT/IB2013/060128 filed Nov. 14, 2013 on behalf of E.T.C. S.R.L. dated: Jan. 23, 2015. 21 pages.
Restriction Requirement for U.S. Appl. No. 14/436,856, filed Apr. 17, 2015 on behalf of Massimo Zambianchi. dated: Dec. 3, 2015. 8 pages.
Non-Final Office Action for U.S. Appl. No. 14/436,856, filed Apr. 17, 2015 on behalf of Massimo Zambianchi. dated: Apr. 5, 2016. 30 pages.
Notice of Allowance for U.S. Appl. No. 14/436,856, filed Apr. 17, 2015 on behalf of Massimo Zambianchi. dated: Jul. 5, 2016. 23 pages.
International Search Report for PCT Application No. PCT/IB2013/060162 filed Nov. 15, 2013 on behalf of E.T.C. S.R.L. dated: Jan. 29, 2014. 4 pages.
Written Opinion of the International Searching Authority for PCT Application No. PCT/IB2013/060162 filed Nov. 15, 2013 on behalf of E.T.C. S.R.L. dated: Jan. 29, 2014. 5 pages.
Notice of Allowance for U.S. Appl. No. 14/423,074, filed Feb. 20, 2015 on behalf of Manuela Melucci. dated: Oct. 4, 2016. 22 pages.
Notice of Allowance for U.S. Appl. No. 14/435,411, filed Apr. 13, 2015 on behalf of Manuela Melucci. dated: Sep. 6, 2016. 10 pages.

ORGANIC SEMICONDUCTOR MATERIAL

CROSS REFERENCE TO RELATED APPLICATIONS

The present application is a Continuation of U.S. application Ser. No. 14/114,892 filed on Oct. 30, 2013 which, in turn is the US national stage of International Patent Application PCT/IB2012/052503 filed on May 18, 2012 which, in turn, claims priority to Italian Patent Application MI2011A000881 filed on May 18, 2011, all of which are hereby incorporated by reference in their entirety.

FIELD

The present invention relates to a novel n-type organic semiconductor material, and semiconductor devices containing said n-type organic semiconductor material.

BACKGROUND

It is known that organic semiconductors are materials into which charge can be reversibly introduced by the application of electromagnetic energy or chemical dopants. The electronic conductivity of these materials lies between that of metals and insulators, spanning a broad range of $10^{-9}$ to $10^{3}$ $\Omega^{-1}cm^{-1}$. As in traditional inorganic semiconductors, organic materials can function either as p-type or n-type. In p-type semiconductors the majority carriers are holes, while in n-type the majority carriers are electrons.

The vast majority of the prior art has focused on the design, synthesis, and structure-property relationships of p-type organic semiconductor materials, including: oligoacenes, fused oligothiophenes, anthradithiophenes, carbazoles, oligophenylenes, and oligofluorenes, some of which have resulted in field-effect transistors with performance superior to amorphous silicon. In contrast, the development of n-type oligomer and polymer semiconductors has lagged behind p-type materials. In fact, compared to the p-type semiconductors, n-type semiconductors are still not fully developed, and the performances are not satisfactory.

Organic semiconductors that possess a high electron affinity are however also required, as both p- and n-channel materials are required for efficient logic circuits and organic solar cells. Indeed, n-type organic field-effect transistors are envisioned as key components of organic p-n junctions, bipolar transistors, and complementary integrated circuits leading to flexible, large-area, and low-cost electronic applications.

A variety of organic semiconductors have been considered in the art as n-type organic semiconductor materials.

Aromatic tetracarboxylic anhydride and their diimide derivatives were reported among the first n-channel materials. Among the materials of this class, perylenetetracarboxylic diimides having fluorinated side chains showed mobilities up to 0.72 $cm^2V^{-1}s^{-1}$, which only slightly decreased upon air exposure. Air stability, packing grain size and morphology of the deposited films as well as electrical performance can be altered by varying side-chain length, insertion of oxygenated groups and degree of fluorination. However, most of the perylene building blocks, due to the structural rigidity and moderate solubility, do not allow readily structural changes limiting the volume of materials accessible.

Other classes of n-type organic materials have been described such as cyanovinyl oligomers, fullerenes.

J. Am. Chem. Soc. 2009, 131, 16616-16617 describes ambipolar charge transport properties of diketopyrrolopyrrole-copolymers.

A benzothiadiazole-diketopyrrolopyrrole copolymer described in Mater. 2010, 22, 47, 5409-5413, shows high and balanced hole- and electron mobilities of 0.35 $cm^2$ $V^{-1}s^{-1}$ and 0.40 $cm^2V^{-1}s^{-1}$, respectively. Larger electron mobilities values up to 0.85 $cm^2V^{-1}s^{-1}$ were achieved in air for electron-only transporting n-type polymer, called poly{[N,N9-bis(2-octyldodecyl)-naphthalene-1,4,5,8-bis (dicarboximide)-2,6-diyl]-alt-5,59-(2,29-bithiophene)}, (Polyera Activink N2200), in a staggered top gate configuration.

N-type semiconductor materials consisting of oligothiophenes bearing fluorinated side groups have been also described in J. Am. Chem. Soc. 2005, 127, 1348 and Angew. Chem. Int. Ed. 2003, 42, 3900. These oligomers showed mobilities up to 0.43 $cm^2V^{-1}s^{-1}$. However, OFETs based on most of these perfluoroaryl and perfluoroalkylaryl substituted materials were unstable in air or suffered from high threshold voltage. Fluorocarbonyl-functionalized oligomers were also described, which showed improved air stability, but lower electron mobilities with respect to fluorinated oligomers.

Oligomers and polymers containing a bithiophene-imide units as inner core have also been described.

For example, J. Am. Chem. Soc. 2008, 130, 9679-9694 describes N-alkyl-2,2'-bithiophene-3,3'-dicarboximide-based homopolymers and copolymers showing p-type or n-type semiconductor behavior depending on the polymeric structure. However, no air-stable devices could be achieved with such materials. In addition, the poor reactivity of the starting dihalogenated bithiophene-imide compounds limits the accessibility of this class of materials.

J. Am. Chem. Soc. 1998, 120, 5355-5362, Tetrahedron Letters 44 (2003) 1563-1565 disclose copolymers containing electron poor 3,4-imido-thienyl blocks alternated to electron rich amino substituted thienyl blocks. No investigation was performed regarding the electrical properties of such copolymers.

N-alkylated poly(dioxopirrolothiophene)s are described in Organic Letters 2004, 6, 19, 3381-3384. However, no proof of an efficient n-type behavior in OFET devices is reported.

Each of the afore mentioned class of materials has poor electrical performances.

WO2008/127029 relates to dioxypirrolo-heterocyclic compounds having the pyrrole moiety fused to the 3,4 position of the thienyl ring and organic electronic devices using said dioxypirrolo-heterocyclic compounds.

Wei Hong et al, "Linear fused dithieno[2,3-b:3'2'-d]thiophene diimides" Organic Letters, vol 13, no. 6, 18 Mar. 2011, pages 1420-1413, discloses a class of linear fully fused dithieno thiophene diimides.

The documents: DE1954550; Ronova Iga A et al: "The effect of conformational rigidity on the initial decomposition temperature of some heterocyclic polyimides", High Performance Polymers, Institute of Physics Publishing, Bristol GB, vol. 14, No. 2, 1 Jan. 2002, pages 195-208; and Gaina C. et al, "Polyimides containing 1,4-dithiine units and their corresponding thiophene 2,3,4,5 tetracarboxylimide units" High Performance Polymers, Institute of physics publishing, Bristol GB, vol. 11, No. 2, 1 Jun. 1999, pages 185-195, disclose polymeric diimmide compounds in which the member connecting the polymer repeating units is the N-imidic substituent. The three last cited documents do not mention any semiconductor property of the compounds therein disclosed.

WO2006/094292 discloses thienopyridine compounds capable of modulating the stability and/or activity of hypoxia inducible factor, pharmaceutical compositions comprising said compounds and chemical intermediates useful for preparing said compounds. Among said chemical intermediates, specific compounds having a 4,6-dioxo-thieno[2,3-c]pyrrole nucleus are disclosed.

EP0467206 discloses specific compounds having a 4,6-dioxo-thieno[2,3-c]pyrrole nucleus and their use as herbicide.

However, WO2006/094292 and EP0467206 do not teach the semiconductor properties of said compounds.

Therefore, there is still the need of n-type organic semiconductor materials or compounds that possess higher electron mobility properties.

SUMMARY

In the present specification and in the claims, the term "n-type organic semiconductor" means a material that, inserted as active layer in a field effect device architecture with a source, a drain and gate control electrodes, shows an electron mobility higher than $10^{-7}$ cm$^2$V$^{-1}$s$^{-1}$.

It is an object of the present invention to provide new organic materials suitable for use as semiconductor material, which is free from said disadvantages. Said object is achieved with a compound whose main features are disclosed in the first claim, a process for the preparation of said compound whose main features are disclosed in claim 10, a use of said compound whose main features are disclosed in claim 11 and an electronic device whose main features are disclosed in claim 14. Other features of said compound are disclosed in claims 2 to 9.

Advantageously, the compounds according to the present invention may be useful as p-type, n-type or ambipolar organic semiconductor material.

Particularly, the compounds according to the present invention possess high electron mobility properties, excellent stability under atmospheric conditions and are accessible through synthetically easy processes.

BRIEF DESCRIPTION OF DRAWINGS

Further advantages and features of the compounds, materials and devices according to the present invention will become clear to those skilled in the art from the following detailed and non-limiting description of an aspect thereof with reference to the attached drawings, wherein.

DETAILED DESCRIPTION

Figure 1A:
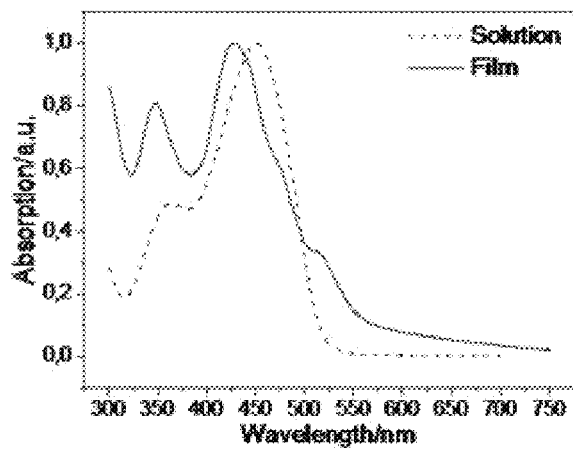
FIG. 1A shows normalized absorption of a solution and film of a compound according to the present invention [2,2'-(2,2'-bithiophene-5,5'-diyl)bis(5-butyl-5H-thieno[2,3-c]pyrrole-4,6-dione)]

According to an aspect of the present invention, a compound of formula (I) or (II) or (III) or (IV) is provided:

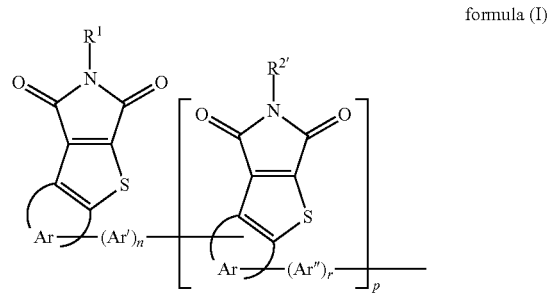

formula (I)

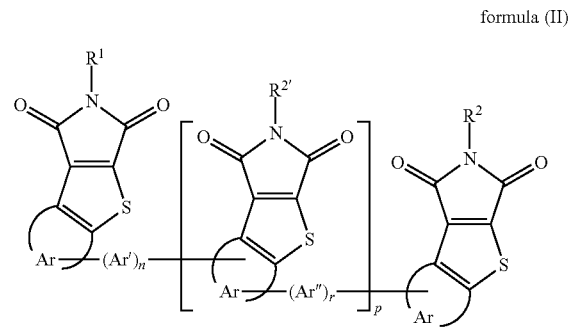

formula (II)

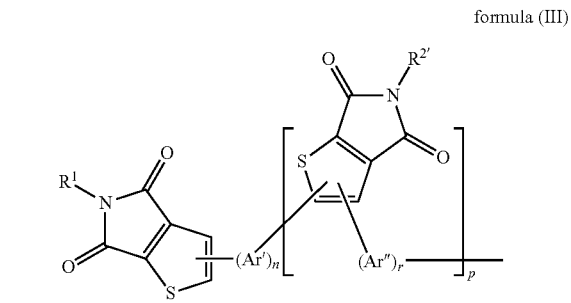

formula (III)

-continued formula (IV)

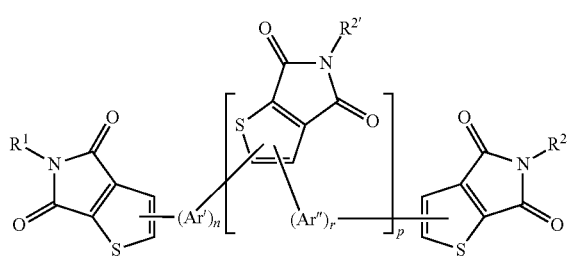

wherein:
$R^1$, $R^2$, $R^{2'}$ independently of each other, are selected in the group consisting of hydrogen, $C_1$-$C_{40}$ linear or branched alkyl groups, $C_1$-$C_{40}$ linear or branched heteroalkyl groups, $C_3$-$C_{40}$ linear or branched cycloalkyl groups, $C_1$-$C_{40}$ linear or branched hydroxyalkyl groups, $C_1$-$C_{40}$ linear or branched alkoxyl groups, $C_1$-$C_{40}$ linear or branched alkylcarboxylic groups, $C_1$-$C_{40}$ linear or branched alkylcarboxamide groups, $C_1$-$C_{40}$ linear or branched alkylsulphonic groups, and $C_1$-$C_{40}$ linear or branched nitrile groups;
Ar is selected in the group consisting of monocyclic aryl groups, polycyclic aryl groups, monocyclic heteroaryl groups and polycyclic heteroaryl groups;
Ar', Ar'', independently of each other, are moieties selected in the group consisting of a monocyclic aryl groups, polycyclic aryl groups, monocyclic heteroaryl groups and polycyclic heteroaryl groups; n, r, independently of each other, are integers between 1 and 50; and p is an integer between 0 and 5; with the exception of compounds of formula A:

formula A

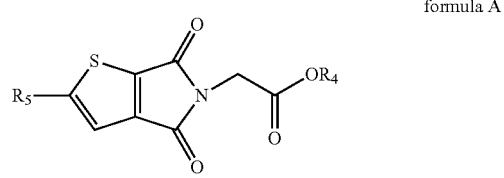

wherein $R_4$ is selected in the group consisting of $C_1$-$C_4$ alkyls; and $R_5$ is selected in the group consisting of monocyclic aryl groups and substituted monocyclic aryl groups; and with the exception of compounds of formula B:

formula B

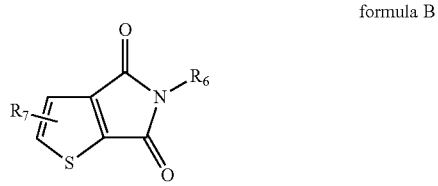

wherein $R_6$ is selected in the group consisting of isopropyl, cyclopropyl and terbutyl groups and $R_7$ is selected in the group consisting of phenyl, 2-fluorphenyl, 3-fluorphenyl, 4-fluorphenyl, 2-chlorphenyl, 3-chlorphenyl, 4-chlorphenyl, 2-methylphenyl, 3-methylphenyl, 4-methylphenyl, 2-trifluoromethylphenyl 3-trifluormethylphenyl, 4-trifluormethylphenyl, 2-methoxyphenyl, 3-methoxyphenyl, 4-methoxyphenyl, 2,4-dichlorphenyl, 2,4,6-trimethylphenyl, 2-thienyl, 3-thienyl, 2-pyridyl, 3-pyridyl, 4-pyridyl.

The value of p is preferably 0, 1 or 2.
The values of n and r are preferably comprised between 2 and 50, more preferably between 2 and 30, even more preferably between 2 and 10.
When p assumes the values of 0, then n is particularly preferably comprised between 2 and 50, more preferably between 2 and 30, even more preferably between 2 and 10.
According to an aspect of the present invention, the compounds of following formulas (Ia), (IIa), (IIIa) and (IVa) are provided, which correspond to those of formulas (I), (II), (III); (IV) wherein p is equal to 0:

formula (Ia)

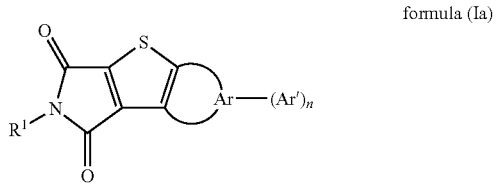

formula (IIa)

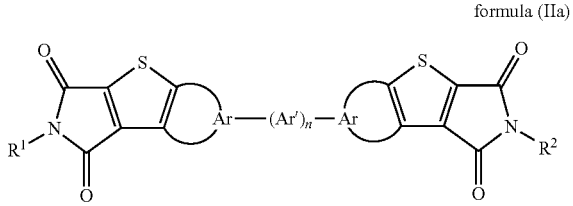

formula (IIIa)

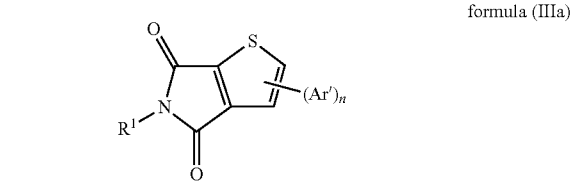

formula (IVa)

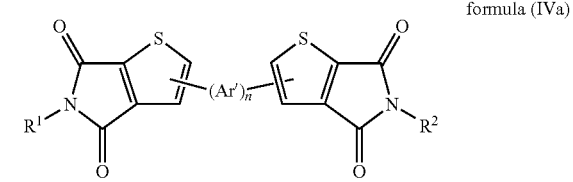

wherein $R^1$, $R^2$, Ar, Ar' and n are as above defined.
In the present description and in the claims, the curved lines in formulas (I), (Ia), (II) and (IIa), connecting the Ar moiety to the imidothiophene unit, indicate that said Ar moiety forms a fused ring system with said imidothiophene unit.
In addition, as usual in chemical drawing practice, in the present description and in the claims the bond line crossing the thiophene double bond in formulas (III), (IIIa), (IV) and (IVa) indicates that the (Ar')$_n$ moiety may be bound to any of the 2 or 3 position in the thiophene ring and is not fused thereto. Preferably, the (Ar')$_n$ moiety is bound to the 2 position of the thiophene ring.
Further, as usual in chemical drawing practice, in the present description and in the claims the bond line crossing the square parenthesis in formulas (I) and (III) is intended to indicate the position of binding of the various repeating units of the polymer. The repeating unit indicated within parenthesis is also one of the terminal units of the polymer.
In formulas (I), (Ia), (II) and (IIa), the (Ar')$_n$ moiety may be bound to any position of the Ar moiety that is fused to the imidothiophene unit.

Preferably, Ar' is a thiophene unit or substituted thiophene unit.
For example, Ar' is a unit selected among the following (a), (b), (c):

(a)

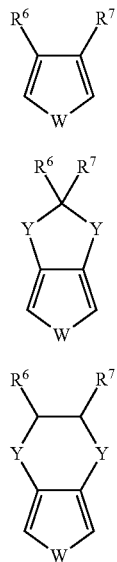

(b)

(c)

wherein W is selected in the group consisting of S, SO and SO$_2$; Y is selected in the group consisting of S, O, NR$^8$; and R$^6$, R$^7$, and R$^8$ independently of each other, are selected in the group consisting of hydrogen, C$_1$-C$_{12}$ linear or branched alkyl groups, C$_1$-C$_{12}$ linear or branched halogenoalkyl groups, C$_3$-C$_{12}$ linear or branched cycloalkyl groups, C$_1$-C$_{12}$ linear or branched hydroxyalkyl groups, C$_1$-C$_{12}$ linear or branched alkoxyl groups, C$_1$-C$_{12}$ linear or branched alkylcarboxylic groups, C$_1$-C$_{12}$ linear or branched alkylcarboxyamide groups, C$_1$-C$_{12}$ linear or branched alkylsulphonic groups, and C$_1$-C$_{12}$ linear or branched nitrile groups.

More preferably, the (Ar')$_n$ moiety is a linear chain of α-linked thiophene units.

In formulas (I), (Ia), (II) and (IIa), the integer n is preferably comprised between 1 and 30, more preferably between 2 and 30, even more preferably between 2 and 10.

The compounds according to the invention wherein n is 2 are characterized by an advantageously high solubility in a number of solvents, for example dichloromethane, dimethyl sulfoxide, tetrahydrofuran.

The Ar moiety fused to the imidothiophene unit of the compounds of formulas (I), (Ia), (II), and (IIa) according to the present invention may be advantageously formed of one, two or three aromatic rings.

Preferably, in formulas (I), (Ia), (II), and (IIa), Ar is selected in the group consisting of the following rings (f), (g), (h), (i), (l), (m), (n), (o), (p):

(f)

(g)

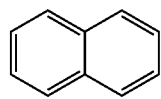

(h)

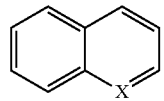

(i)

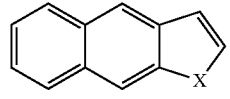

(l)

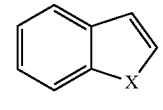

(m)

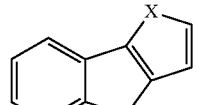

(n)

(o)

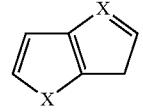

(p)

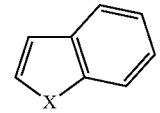

wherein X is selected in the group consisting of S, O, Si, Se, NR$^3$,

R$^3$, is selected in the group consisting of C$_1$-C$_{12}$ linear or branched alkyl groups, C$_1$-C$_{12}$ linear or branched halogenoalkyl groups, C$_3$-C$_{12}$ linear or branched cycloalkyl groups, C$_1$-C$_{12}$ linear or branched hydroxyalkyl groups, C$_1$-C$_{12}$ linear or branched alkoxyl groups, C$_1$-C$_{12}$ linear or branched alkylcarboxylic groups, C$_1$-C$_{12}$ linear or branched alkylcarboxyamide groups, C$_1$-C$_{12}$ linear or branched alkylsulphonic groups, and C$_1$-C$_{12}$ linear or branched nitrile groups.

Preferably, R$^1$, R$^2$, independently of each other, are selected in the group consisting of C$_1$-C$_{12}$ linear or branched alkyl groups, C$_1$-C$_{12}$ linear or branched heteroalkyl groups, C$_3$-C$_{12}$ linear or branched cycloalkyl groups, C$_1$-C$_{12}$ linear or branched hydroxyalkyl groups, C$_1$-C$_{12}$ linear or branched alkoxyl groups, C$_1$-C$_{12}$ linear or branched alkylcarboxylic groups, C$_1$-C$_{12}$ linear or branched alkylcarboxyamide groups, C$_1$-C$_{12}$ linear or branched alkylsulphonic groups, and C$_1$-C$_{12}$ linear or branched nitrile groups.

More preferably, R$^1$, R$^2$, independently of each other, are selected in the group consisting of C$_1$-C$_{12}$ linear or branched saturated alkyl groups, C$_1$-C$_{12}$ linear or branched fluoroalkyl groups, C$_1$-C$_{12}$ linear or branched heteroalkyl groups comprising a heteroatom selected among O, S, N.

Preferably, in formulas (II), (IIa), (IV) and (IVa), R$_1$ is the same as R$_2$. According to a preferred aspect of the invention, a linear α-linked oligothiophene di-imide compound of formula (V) is provided:

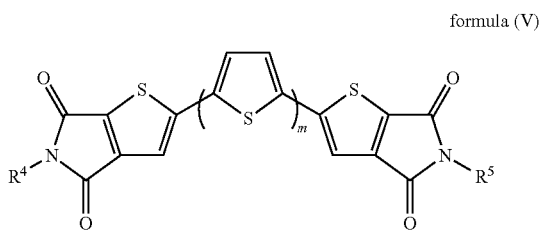

formula (V)

wherein $R^4$, $R^5$ are selected in the group consisting of $C_1$-$C_8$ linear or branched saturated alkyl groups, $C_1$-$C_8$ linear or branched fluoroalkyl groups, $C_1$-$C_8$ linear or branched heteroalkyl groups comprising a heteroatom selected among O, S, N; and m is an integer between 1 and 50.

More preferably, in compound of formula (V), m is comprised between 1 and 30, more preferably between 2 and 30, even more preferably, m is comprised between 2 and 10.

According to a more preferred aspect of the invention, a compound is provided having formula (VI):

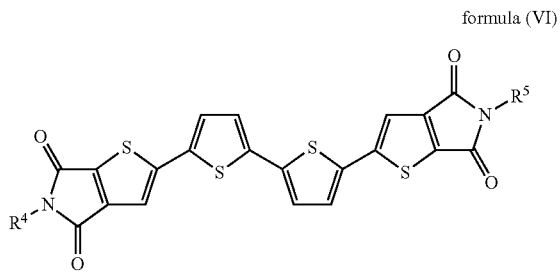

formula (VI)

wherein $R^4$, $R^5$ are as above defined with reference to formula (V).

According to another preferred aspect of the invention, a compound is provided having formula (VII):

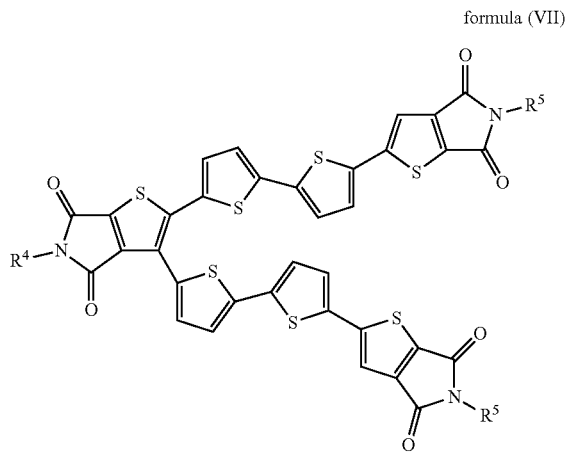

formula (VII)

wherein $R^4$, $R^5$ are as above defined with reference to formula (V).

As it may well be understood, the compound of formula (VII) derives from general formula (IV) wherein p is equal to 1; n and r are equal to 2; Ar' and Ar" are thiophene, $R^1$ and $R^2$ are $R^5$; and $R^{2'}$ is $R^4$.

Without wishing to limit the present invention to any theory, it is believed that the imido-thiophene moiety allows for the combination of the strong electron-withdrawing effect of the carboxylic groups, which contributes in lowering the LUMO energy level of the final oligomer, to the chemical versatility, robustness and plasticity of the thienyl ring. This allows the realization of novel α-conjugated materials with high electron affinities comparable to the currently more performing n-type semiconducting organic materials.

Among the main advantages of such compounds with respect to other classes of n-type materials are to be mentioned the easy accessibility and structural versatility.

As a matter of fact, the imide moieties can be easily fused to the thienyl ring, as described below. The imido-thiophene moiety can easily be mono- or dihalogenated to realize linear oligomers.

Finally N-substitution, particularly with linear, branched alkyl, heteroalkyl and perfluoroalkyl chains can be easily achieved by standard chemistry and exploited to tune solubility, self-organization and optoelectronic properties.

The advantage of the compounds of formulas (I) and (II), wherein the imido-thiophene block is inserted into fused heterocycles with high degree of α-conjugation and planar structure, is that further tuning of the electronic levels as well as the morphology and optoelectronic properties of the final oligomers are possible.

The thiophene-imide moiety can be coupled to selected π-conjugated cores by cross-couplings under conventional or microwave-assisted methods as described below.

The easy accessibility of the compounds according to the invention also allows an easy modification of the oligomer size, and degree and type of molecular functionalization, which in turn permits to tailor the compounds properties as a function of the particular requirements of the desired application.

The compounds according to the present invention can be obtained with electronic level of purity by chromatography, crystallization and sublimation, with unambiguous molecular structure determination through classic analytical methods.

Contrarily to the thiophene-3,4-imide polymers, bithiophene-imide polymers and perylene tetracarboxylic diimide systems according to the prior art, this class of materials can be prepared with high reproducibility from batch to batch, which is crucial to achieve devices with reproducible responses. In addition, they can be adapted to solution processing by inserting tailored alkyl or alkoxy-chains as N-substituents.

Another advantage of the compounds according to the present invention consists in its high self-organization capability and order in thin films, due to their chemical structure comprising an imide moiety as alpha-end-substituent rather than beta inner substituent.

According to still another aspect of the invention, it is provided a process for the production of a compound according to the invention, wherein the process comprises: subjecting a reaction mixture comprising a reaction medium and an halogenated aromatic halide to: a Stille coupling reaction with an organtin compound; or to a Suzuki coupling reaction with an organoboron compound.

The processes according to the present invention are preferably catalized by palladium.

The compounds according to the invention of formulas (I), (II), (III), and (IV) may be obtained starting from a dihalogenated aromatic halide, such as in the following Schemes 1 and 2:

Scheme 1
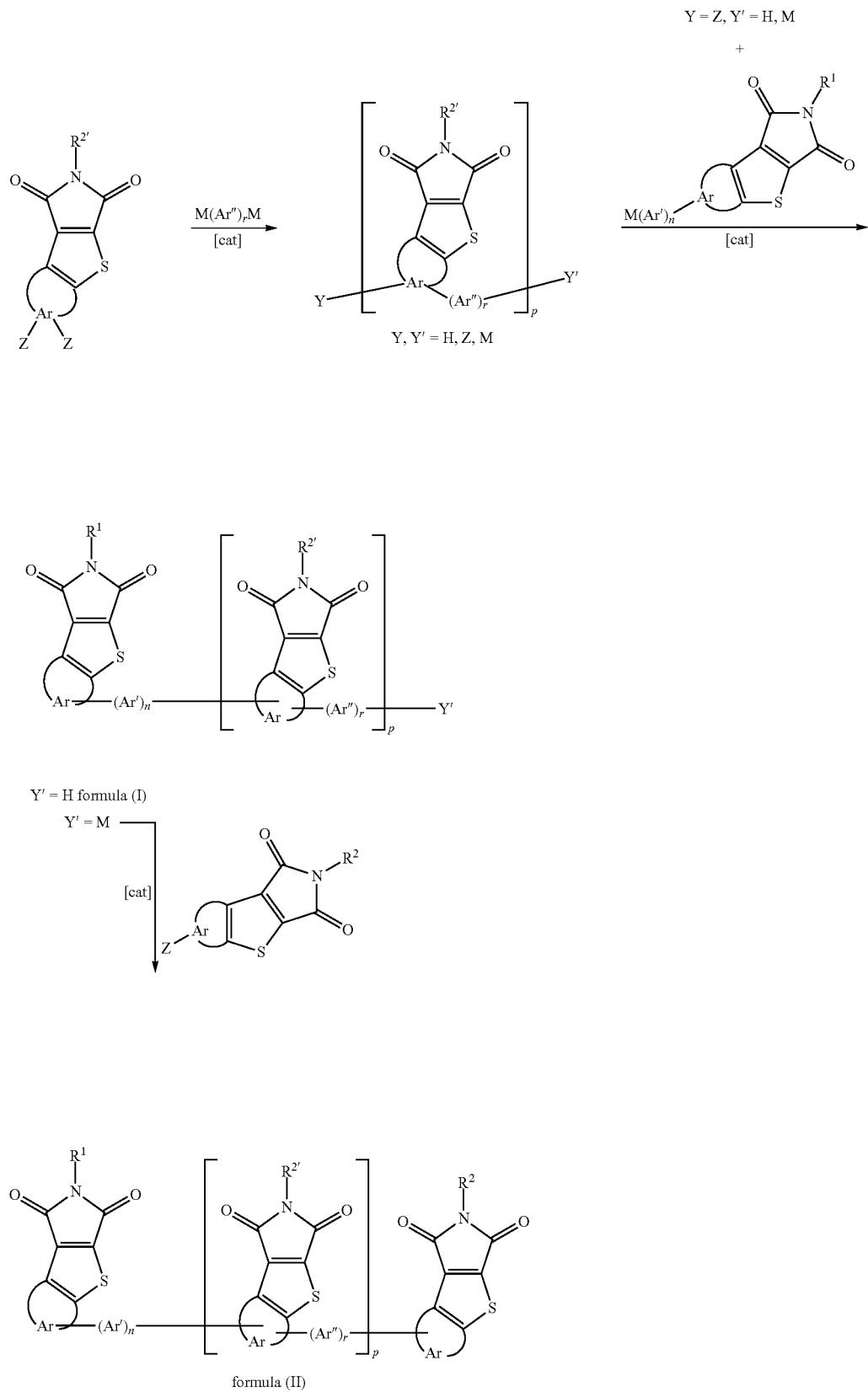

Scheme 2
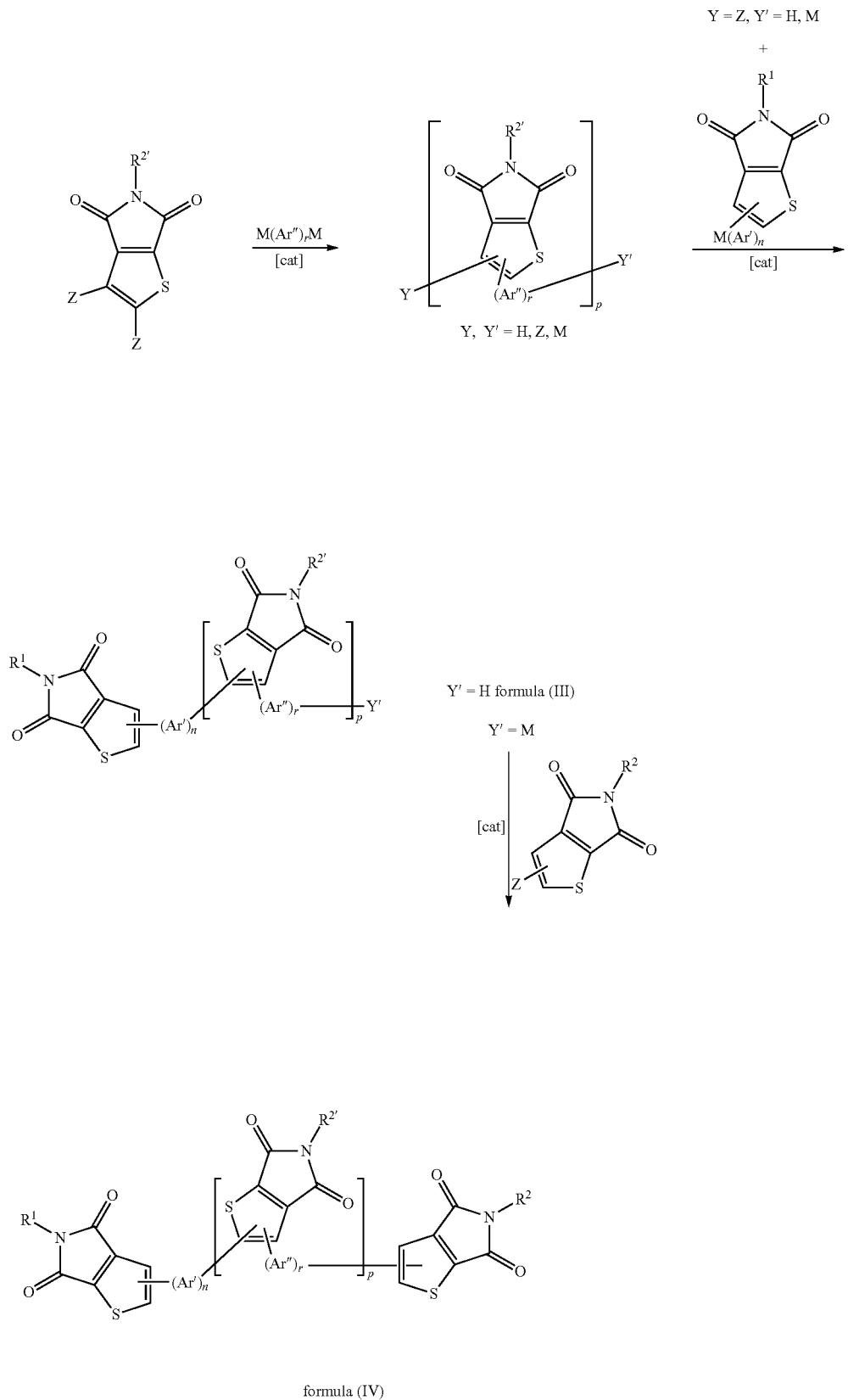
formula (IV)

wherein Z is selected among halogen atoms, such as Br, I; M is an organometal compound such as $B(OR')_2$ and $SnR''_3$; and [cat] is a palladium based catalyst.

The compounds of formulas (Ia), (IIa), (IIIa) and (IVa) may be obtained according to the present invention by means of processes as outlined in the following Schemes 3 and 4:

the solid state, thus the final functional properties. In the above schemes, the symmetry of the final compounds can be controlled by changing the synthetic approach. Cross-coupling reaction between mono-halogenated thiophene-imide unit and monometallic species lead to asymmetric systems (Ia) and (IIIa). On the other hand, by using bimetallic species

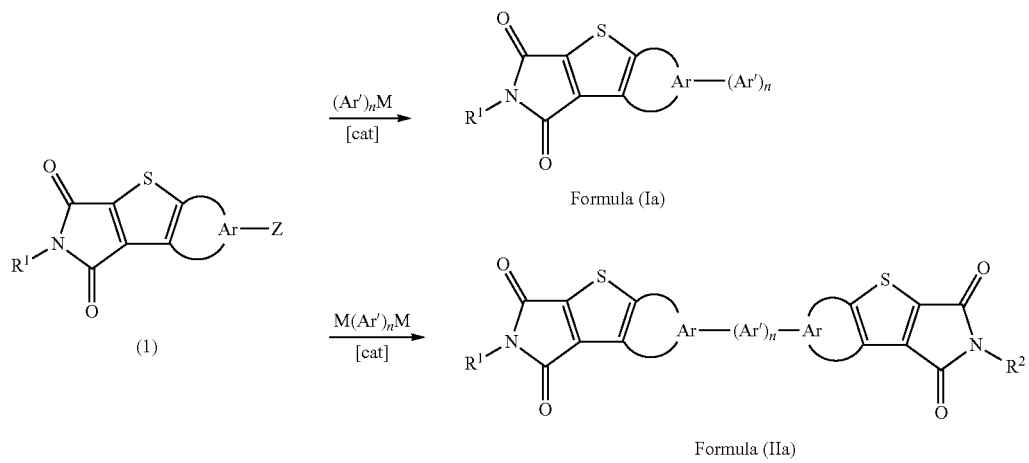

Scheme 3

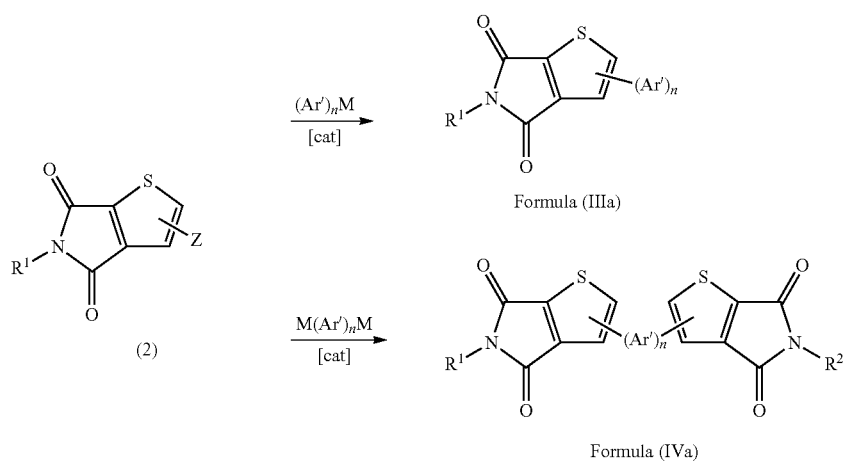

Scheme 4 wherein Z is selected among halogen atoms, such as Br, I; M is an organometal compound such as $B(OR')_2$ and $SnR''_3$; and [cat] is a palladium based catalyst. For example, tetrakis triphenylphosphine palladium (0) can be used as catalyst.

The molecular symmetry of the compounds affects the self-organization motifs and morphology of the molecules in a symmetric system can be obtained, provided that the N-substituting radical $R^1$ and $R^2$ are the same.

In detail, the synthesis of a preferred compound 12, of formula (VI) according to the present invention, is outlined in the following Scheme 5.

Scheme 5

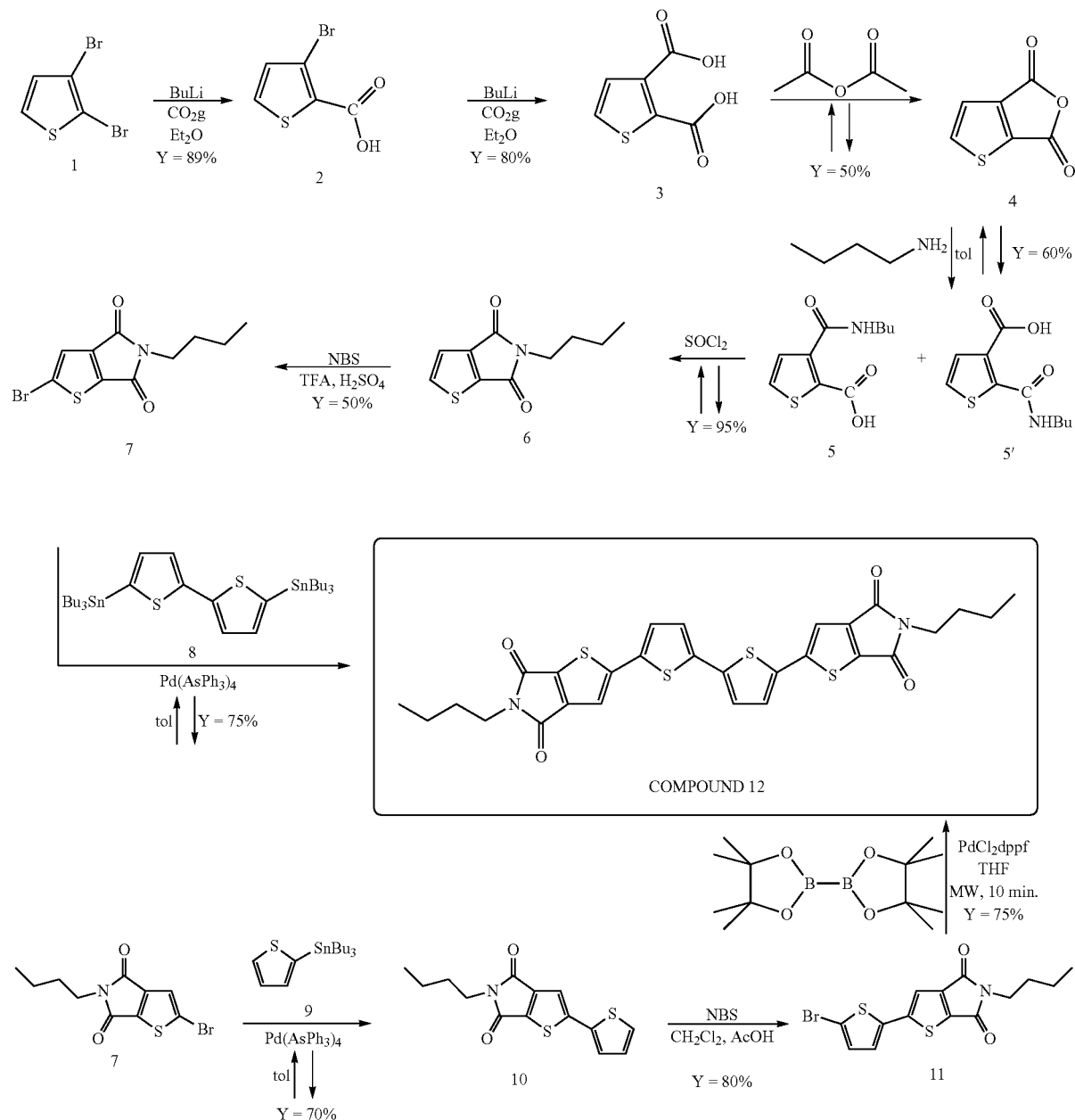

This scheme outlines the preparation of compound 12 according to the present invention, a thiophene based oligomer in which the aromatic core Ar' consists of a 2,2'-bithiophene, the N-substituent is a n-butyl group and the terminals are symmetric imide moieties. Two synthetic routes to the target oligomer have been developed and are depicted the above Scheme 6. The first method is based on the Stille cross coupling reaction between a bistannyl-bithiophene 8 and the brominated thiophene-imide block 7 under conventional heating. The second route consists of microwave assisted one-pot borylation-Suzuki coupling starting from the brominated thiophene-imide-thiophene dimer. The latter method affords higher yields in only 10 minutes of microwave irradiation (P=300 W, T=80° C.) and appears more convenient also in terms of product purity since no-Sn side-products, requiring tedious purification steps, are formed.

In detail, the thiophene-imide starting unit 6 can be prepared by the corresponding anhydride 4, following prior art processes. Bromination of 6 can be achieved under harsh conditions by using a mixture of trifluoroacetic and sulphuric acids. Following Stille cross-coupling of compound 7 with tributhylstannilthiophene 9, leads to the dimer 10 in satisfying yield, which can be then brominated under conventional halogenations reaction conditions to give 11 in satisfying yield. By the first outlined method, the target oligomer compound 12 can be then prepared by one-pot microwave assisted borylation/Suzuki coupling reactions by using bispinacol borate as borylating agent and PdCl$_2$dppf as Pd [0] source.

Compound 12 shows good solubility in common organic solvents (i.e. dichloromethane, toluene, tetrahydrofuran) allowing for solution processing. The purification to electronic grade material can be achieved by repeated vacuum sublimation.

The compounds of formula (VII) may be obtained according to the following Scheme 6:

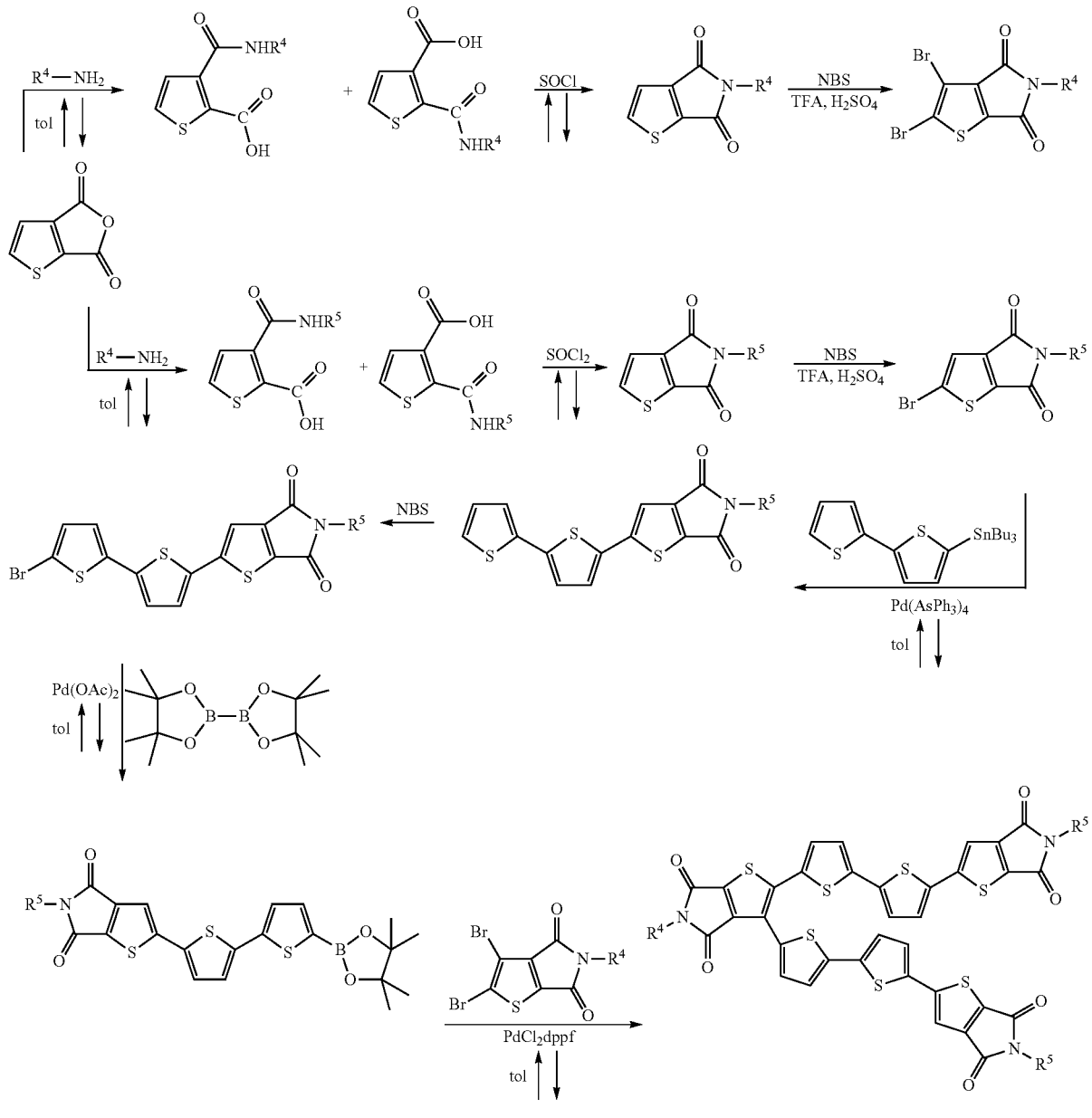

Formula (VII)

In another aspect thereof, the present invention relates to a semiconductor material, comprising at least one compound according to formulas (I); (II); (III); or (IV). Preferably, said semiconductor material comprises at least one compound according to formulas (Ia); (IIa); (IIIa); or (IVa). More preferably, said semiconductor material, comprises at least one compound according to formulas (V), (VI) or (VII).

In an embodiment thereof, said semiconductor material comprises compound 12.

According to another aspect, the invention relates to an electronic device comprising a semiconductor layer in contact with a number of electrodes, wherein the semiconductor layer includes at least one compound according to formulas (I); (II); (III); or (IV). Preferably, said semiconductor layer comprises at least one compound according to formulas (Ia); (IIa); (IIIa); or (IVa). More preferably, said semiconductor layer, comprises at least one compound according to formulas (V), (VI) or (VII).

In an embodiment thereof, said semiconductor layer comprises compound 12.

Preferably, said electronic device comprising a semiconductor layer including the compounds according to the present invention is selected among optical devices, electrooptical devices, field effect transistors, integrated circuit, thin film transistors, organic light-emitting devices, and organic solar cells.

Particularly, thin films of the thiophene-imide based materials according to the invention can be used as active layers in OFETs and OLET devices as demonstrated in the following examples. They can be used as electron- or hole-transporting layer or ambipolar transporters in single layer OFET, as multifunctional electron- and hole-transporting and light emitting layer in single layer OLET, and as hole or electron transporting layer in multi-layer OLET.

Finally, applications of compounds and materials according to the present invention in organic photovoltaics can be envisaged.

In the following examples, microwave experiments were carried out in a Milestone Microsynth Labstation operating at 2450 MHz monitored by a proprietary control unit. The oven was equipped with magnetic stirring, pressure and temperature sensors. Reactions were performed in a glass vessel (capacity 10 mL) sealed with a septum. The microwave method was power controlled and the samples were irradiated with the required power output (setting at the maximum power) to achieve the desired temperature. All $^1$H NMR, $^{13}$C NMR spectra were recorded at room temperature on a Varian Mercury-400 spectrometer equipped with a 5-mm probe. Flash chromatography was carried out using silica gel (200-300 mesh ASTM). Analytical thin layer chromatography (TLC) was carried out using 0.2 mm sheets of silica gel 60 F254 and the visualization accomplished by UV light (356 nm and 254 nm). Melting points were determined on a Kofler bank apparatus and are uncorrected.

Example 1: Preparation of 3-bromothiophene-2-carboxylic acid

To a solution of nBuLi (2.5 M, 0.055 mol, 22 ml) in dry Et$_2$O (15 ml) at −78° C. in N$_2$ atmosphere, 2,3-dibromothiophene (12.1 g, 0.025 mol) was added drop wise. After ten minutes from the addition of the last portion, gaseous CO$_2$ was fluxed into the solution and the formation of a white precipitate was immediately observed. The suspension was stirred for additional 30 minutes at −78° C., then was allowed to reach room temperature. The reaction was quenched by adding milliQ H$_2$O, then the aqueous phase was extracted by NaOH 10% (3×50 ml). Subsequently, HCl 6 N was added and the precipitate formed was collected by filtration. Re-crystallization from EtOH (50 ml) and H$_2$O (200 ml) and finally, drying under vacuum furnished 9.23 g of a white powder.

M.p. 191° C., MS (70 eV, EI): m/z 208 (M.−1), $^1$H NMR (CDCl$_3$): δ □ppm=7.81 (d, 1H, J=5.2 Hz), 7.19 (d, 1H, J=5.2 Hz)$^{13}$C NMR (CDCl$_3$): δ ppm=117.6, 133.8, 134.6, 162.6, 207.6.

Example 2: Preparation of thiophene-2,3-dicarboxylic acid

This compound was prepared according to the procedure used for the synthesis of 3-bromothiophene-2-carboxylic acid, starting from 5.18 g (0.025 mol) of 3-bromothiophene-2-carboxylic acid and 30 ml (0.075 mol) of nBuLi. Recrystallization from EtOH/H$_2$O afforded thiophene-2,3-dicarboxylic acid as white powder (Y=80%) M.p. 268° C., MS (70 eV, EI): m/z 278 (M.−1), $^1$H NMR (CDCl$_3$+CS$_2$, TMS): δ □ppm=7.89 (d, 1H, J=5.2 Hz), 7.71 (d, 1H, J=5.2 Hz).

Example 3: Preparation of thiophene-2,3-dicarboxylic anhydride

Thiophene-2,3-dicarboxylic acid (760 mg, 5 mmol) was dissolved in 20 ml of acetic anhydride and the solution was stirred overnight at 140° C. The reaction mixture was subsequently concentrated to a pale brown solid which was recrystallized from toluene to afford thiophene-2,3-dicarboxylic anhydride (Y=50%) as pale yellow crystals.

M.p. 147.5° C., MS (70 eV, EI): m/z 155 (M.−1), $^1$H NMR (CDCl$_3$): δ □ ppm=8.43 (d, 1H, J=4.8 Hz), 7.58 (d, 1H, J=4.8 Hz). 13C NMR (CDCl$_3$): δ ppm=123.3, 143.3, 145.4, 147.4, 158.7, 159.5, 206.9.

Example 4: Preparation of 2-butylcarbamoylthiophene-3-carboxylic acid, and 3-butylcarbamoylthiophene-2-carboxylic acid A solution of thiophene-2,3-dicarboxylic anhydride (171 mg, 1 mmol) and n-butylamine (77 mg, 1.05 mmol) in 15 ml of toluene was refluxed for 24 h. The crude products were collected by filtration of the cold reaction mixture. Another portion was achieved by washing the filtrate with 5% hydrochloric acid and then evaporating the solvent. Recrystallization from toluene afforded a mixture of 2-butylcarbamoylthiophene-3-carboxylic acid and 3-butylcarbamoylthiophene-2-carboxylic acid in 60% yield as white solid which was used for cyclization without further purification.

MS (70 eV, EI): m/z 227 (M.−1), $^1$H NMR (CDCl$_3$): δ □ppm=7.76 (d, 1H, J=5.2 Hz), 7.56 (d, 1H, J=5.2 Hz), 7.5 (1H, broad), 7.0 (1H, broad, —OH), 7.39 (m, 2H, —OH), 3.49 (m, 2H), 3.0 (1H, broad —NH), 1.8 (broad, 1H, —NH), 1.64 (m, 2H), 1.4 (m, 2H), 0.96 (m, 3H). $^{13}$C NMR (CDCl$_3$, TMS): δ ppm=131.5, 126.5, 40.5, 31.1, 20.1, 13.7.

Example 5: Preparation of 5-butylthieno[2,3-c]pyrrole-4,6-dione

A solution of 2-butylcarbamoylthiophene-3-carboxylic acid, and 3-butylcarbamoylthiophene-2-carboxylic acid (136 mg, 0.6 mmol) in 12 ml of thionyl chloride was refluxed for 3 h. The reaction mixture was concentrated to a yellow oil Flash chromatography on silica gel, by using petroleum ether:CH$_2$Cl$_2$:AcOEt=6:2:2, afforded 5-Butylthieno[2,3-c]pyrrole-4,6-dione as dark yellow oil (124 mg, Y<99%). MS (70 eV, EI): m/z 209 (M.−1), $^1$H NMR (CDCl$_3$, TMS): δ □ppm=7.74 (d, 1H, J=4.8 Hz), 7.27 (d, 1H, J=5.2 Hz), 3.57 (t, 2H), 1.59 (m, 2H), 1.33 (m, 2H), 0.91 (t, 3H). $^{13}$C NMR (CDCl$_3$, TMS): δ ppm=163.8, 162.7, 144.6, 140.7, 137.2, 120.9, 38.1, 30.7, 19.9, 13.5.

Example 6: Preparation of 2-bromo-5-butyl-5H-thieno[2,3-c]pyrrole-4,6-dione

5-Butylthieno[2,3-c]pyrrole-4,6-dione (123 mg, 0.59 mmol) was dissolved in 4 ml of a 1:3 mixture of concentrated sulfuric acid and trifluoroacetic acid. NBS (116 mg, 0.65 mmol) was added in 3 portions over 3 hs and the reaction mixture was stirred at room temperature over-night. The brown solution was then diluted with 40 ml of water and extracted with dichloromethane. The organic phase was dried over anhydrous magnesium sulfate and evaporated to afford the crude product as a brown oil. Purification by column chromatography using silica gel and petroleum ether:AcOEt (95:5) as eluent followed by recrystallization from aqueous ethanol gave the desired 2-bromo-5-butyl-5H-thieno[2,3-c]pyrrole-4,6-dione in 50% yield.

$^1$H NMR (CDCl$_3$): δ ppm=7.29 (s, 1H), 3.57 (t, 4H), 1.6 (m, 24H), 1.33 (m, 4H), 0.92 (t, 3H).

Example 7: Preparation of 5-butyl-2-(thiophene-2-yl)-5H-thieno[3,2-c]pyrrole-4,6-dione To a refluxing toluene solution (6 ml) of 2-bromo-5-butyl-5H-thieno[2,3-c]pyrrole-4,6-dione (101 mg, 0.35 mmol), in situ-prepared Pd(AsPh$_3$)$_4$ (5 mol %, i.e. 9.0 mg of Pd$_2$dba$_3$ and 21.4 mg of AsPh$_3$π at 80° C. under N$_2$ atmosphere, 2-(tributylstannyl)thiophene (144 mg, 0.38 mmol) in toluene (2 ml), was added dropwise. The solution was refluxed for 2 h then the solvent was removed under vacuum and the crude product purified by flash chromatography on silica gel by using increasing amounts of EtOAc in petroleum ether as eluent. 5-Butyl-2-(thiophene-2-yl)-5H-thieno[3,2-c]pyrrole-4,6-dione was obtained as bright yellow microcrystals (76 mg, 75%).

M.p. 143° C., MS (70 eV, EI): m/z 291 (M.−1), $^1$H NMR (CDCl$_3$, TMS/ppm): 7.38 (dd, 3J=5.2 Hz, 4J=1.2 Hz, 1H), 7.32 (dd, 3J=3.6 Hz, 4J=1.2 Hz, 1H), 7.31 (s, 1H), 7.08 (dd, 3J=5.2 Hz, 3J=3.6 Hz, 1H), 3.60 (t, 2H), 1.63 (m, 2H), 1.36 (m, 2H), 0.94 (t, 3H). $^{13}$C NMR (CDCl$_3$, TMS/ppm): 164.0, 162.9, 145.1, 143.3, 137.4, 135.2, 128.3, 127.2, 126.1, 116.6, 38.3, 30.8, 20.0, 13.6.

Example 8: Preparation of 2-(5-bromothiophen-2-yl)-5-butyl-5H-thieno[3,2-c]pyrrole-4,6-dione 5-Butyl-2-(thiophene-2-yl)-5H-thieno[3,2-c]pyrrole-4,6-dione (70 mg, 0.24 mmol) was dissolved in 4 ml of a 1:1 mixture of dichloromethane and acetic acid solution. NBS (43 mg, 0.24 mmol) was then added in darkness, and the reaction mixture was stirred at room temperature over-night. The yellow solution was then diluted with 10 ml of water, extracted with dichloromethane, washed with 10% NaHCO$_3$, and water. The organic phase was dried over anhydrous sodium sulfate and evaporated to afford compound 10 as a bright yellow solid (88 mg, 99%) which was used without further purification.

M.p. 170° C., MS (70 eV, EI): m/z 370 (M.−1), $^1$H NMR (CDCl$_3$, TMS/ppm): 7.24 (s, 1H), 7.07 (d, 3J=3.6 Hz, 1H), 7.04 (d, 3J=3.6 Hz, 1H), 3.60 (t, 2H), 1.62 (m, 2H), 1.35 (m, 2H), 0.94 (t, 3H). $^{13}$C NMR (CDCl3, TMS/ppm) 163.8, 162.7, 148.8, 145.1, 137.8, 136.5, 131.1, 126.2, 116.8, 114.4, 38.3, 30.8, 20.0, 13.6.

Example 9: Preparation of 2,2'-(2,2'-bithiophene-5,5'-diyl)bis(5-butyl-5H-thieno[2,3-c]pyrrole-4,6-dione)

Route 1: To a refluxing toluene solution (8 ml) of 2-bromo-5-butyl-5H-thieno[2,3-c]pyrrole-4,6-dione (101 mg, 0.35 mmol), in situ-prepared Pd(AsPh$_3$)$_4$ (6 mol %, i.e. 11.3 mg of Pd$_2$dba3 and 26.7 mg of AsPh3] at 80° C. under N$_2$ atmosphere, 5,5'-bis(tributylstannyl)-2,2'-bithiophene, 8 (155 mg, 0.26 mmol) in toluene (2 ml), was added drop wise. The solution was refluxed for 24 h then the solvent was removed under vacuum and the crude product purified by flash chromatography on silica gel by using a solution of pet. eth.:CH$_2$Cl$_2$=50:50→pet. eth.:CH$_2$Cl$_2$:AcOEt=45:45:10 as the eluent. The target compound was obtained as a strong red powder (76 mg, 75%) M.p. 294° C., MS (70 eV, EI): m/z 580 (M.−1), absorption maximum, 449 nm, emission maximum, 570 nm in DCM; $^1$H NMR (CD$_2$Cl$_2$, TMS/ppm): 7.36 (s, 2H), 7.32 (d, 3J=4.0 Hz, 2H), 7.04 (d, 3J=4.0 Hz, 2H), 3.60 (t, 4H), 1.63 (m, 4H), 1.36 (m, 4H), 0.96 (t, 6H). Anal. Calcd for C$_{28}$H$_{24}$N$_2$O$_4$S$_4$ (580.76): C, 57.91; H, 4.17. Found: C, 57.99; H, 4.27.

Route 2: A mixture of 5-butyl-2-(thiophene-2-yl)-5H-thieno[3,2-c]pyrrole-4,6-dione (37.0 mg, 0.1 mmol), bis (pinacolato)diboron (15.2 mg, 0.06 mmol), (dppf)PdCl$_2$ (4.1 mg, 0.005 mmol), NaHCO$_3$ (21.0 mg, 0.25 mmol) in THF/water 5:1 (3.6 mL) was irradiated with microwaves at 80° C. for 20 min. After cooling to room temperature, a TLC monitoring showed the absence of starting material 10. After evaporation of the solvent in vacuo, the crude mixture was washed in pentane to remove the excess of boron, then dissolved in toluene and filtered over silica gel to remove the catalyst. Recrystallization from hot toluene gave compound 11 in 75% yield. M.p. 296° C., Anal. Calcd for C$_{28}$H$_{24}$N$_2$O$_4$S$_4$ (580.76): C, 57.91; H, 4.17. Found: C, 57.95; H, 4.20.

Example 10: Registration of Absorption, Emission and Electrochemical Properties of 2,2'-(2,2'-bithiophene-5,5'-diyl)bis(5-butyl-5H-thieno[2,3-c]pyrrole-4,6-dione)

UV-vis and fluorescence (PL) spectra of 2,2'-(2,2'-bithiophene-5,5'-diyl)bis(5-butyl-5H-thieno[2,3-c]pyrrole-4,6-dione) (compound 12) were recorded with a JASCO V-550 spectrophotometer. Photoluminescence was excited using a CW He—Cd laser at 440 nm with 20 mW power. PL excitation was truncated with a GG450 cut-off filter without modulating the PL spectra. PL emission was collected with a calibrated optical multichannel analyzer (PMA-11, Hamamatsu).

Redox potentials of 2,2'-(2,2'-bithiophene-5,5'-diyl)bis(5-butyl-5H-thieno[2,3-c]pyrrole-4,6-dione), 12 have been measured at room temperature on 1.5 mmol·l$^{-1}$ solution in CH$_2$Cl$_2$ (Carlo Erba RPE, distilled over P$_2$O$_5$ and stored under Ar pressure) with 0.1 mmol·l$^{-1}$ (C$_4$H$_9$)$_4$NClO$_4$ (Fluka, puriss. crystallized from CH$_3$OH and vacuum dried). After Ar bubbling, CVs were performed at scan rates within 0.01 and 0.2 V·s$^{-1}$, in a home-made three compartment glass cell under Ar pressure, by using an AMEL electrochemical system model 5000. Working electrode was semi-spherical Pt, auxiliary electrode was a Pt wire, and reference electrode was aqueous KCl Saturated Calomel Electrode (SCE). The standard potentials have been evaluated as the average of the potentials of the maxima of the forward and backward waves.

Figure 1B:
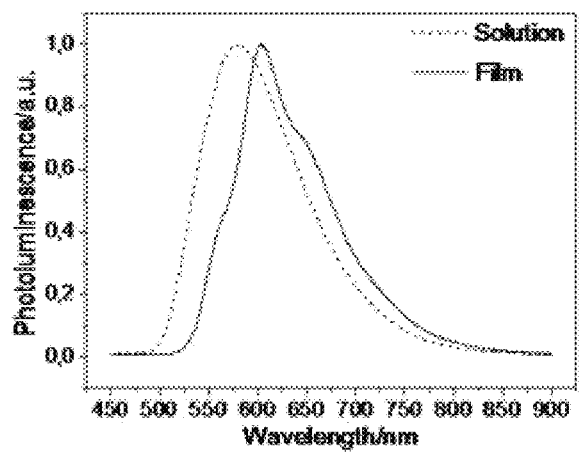
FIG. 1B shows normalized emission of a solution and film of a compound according to the present invention [2,2'-(2,2'-bithiophene-5,5'-diyl)bis(5-butyl-5H-thieno[2,3-c]pyrrole-4,6-dione)]

The normalized absorption and emission spectra of 2,2'-(2,2'-bithiophene-5,5'-diyl)bis(5-butyl-5H-thieno[2,3-c]pyrrole-4,6-dione) (compound 12) in 4×10$^{-5}$ CH$_2$Cl$_2$ solution and 100 nm thick film are shown in FIGS. 1A, 1B respectively. The solution and film spectra were similar, suggesting high molecular planarity and rigidity. The absorption maximum is located at about λmax=440 nm in solution and λmax=470 nm in film, strongly red shifted with respect to dihexyl substituted quaterthiophene (λmax=401 nm) and diperfluorohexyl quaterthiophene (λmax=398 nm) highlighting the strong electron-withdrawing feature of the diimide moieties. Similarly, the emission maximum λem is located at 579 nm (λexc=449 nm) in solution and λem=603 nm in film, strongly red-shifted with respect to the alkyl substituted analogue.

Figure 1C:
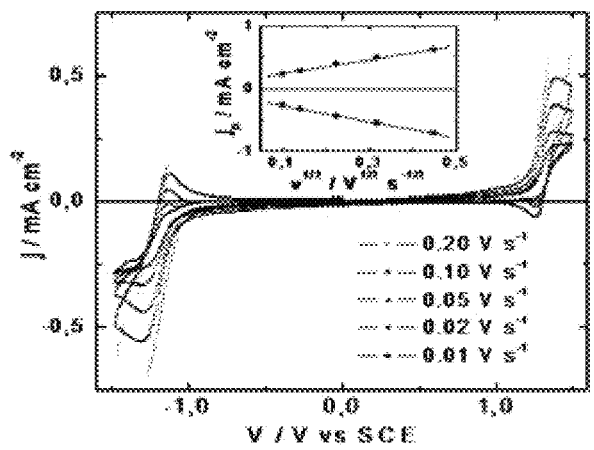
FIG. 1C shows the CV curves for said compound according to the present invention [2,2'-(2,2'-bithiophene-5,5'-diyl)bis(5-butyl-5H-thieno[2,3-c]pyrrole-4,6-dione)]

The cyclic voltammetry (CV) in CH$_2$Cl$_2$ 0.1 mol l$^{-1}$ (C$_4$H$_9$)$_4$NClO$_4$, of 2,2'-(2,2'-bithiophene-5,5'-diyl)bis(5-butyl-5H-thieno[2,3-c]pyrrole-4,6-dione) (compound 12) and peak currents as a function of the square rote of the scan rate is shown in FIG. 1C. At scan rate $v=0.2$ Vs$^{-1}$, the potentials of the reduction and oxidation wave maxima resulted −1.33 and 1.42 V vs. SCE, respectively. The standard potentials resulted E°red=−1.21 V and E°ox=1.32 V vs. SCE that gives an electrochemical energy gap Egelec=2.53 eV (close to the Egopt=2.4 eV) and a HOMO energy value of −6 eV and a LUMO one of −3.4 eV. Correlation coefficient of peak currents vs. $v^{-1/2}$ linear fits are >0.997 and the differences of the slopes for the oxidation and reduction peaks are <15%, the resulting diffusion coefficient is $2.9 \times 10^{-3}$ cm$^2$ s$^{-1}$.

Spectroscopic and ciclovoltammetry data are summarized in Table 1 and are compared to those of hexyl substituted quaterthiophene (T4Hex) and to those of the known thiophene-based n-type organic semiconductor α,ω-diperfluorohexyltetrathiophene (DFH-4T).

Table 1 shows that the ionization potential of the new compound 2,2'-(2,2'-bithiophene-5,5'-diyl)bis(5-butyl-5H-thieno[2,3-c]pyrrole-4,6-dione) appears close to that of DFH-4T but the electron affinity is likely 0.3 eV higher. Consequently, the energy-gap results smaller.

gated by combining both differential scanning calorimetry (DSC) analysis and hot stage polarized microscopy (POM). Differential scanning calorimetry (DSC) analysis was performed by using a Thass DSC-XP-10 instrument under atmospheric conditions.

Hot stage polarized microscopy (POM) was performed by using a Nikon Eclipse 80i optical microscope was used for optical measurements. The images were recorded with a digital color camera Nikon Coolpix 5400. Glass substrate were furnished by Knittel gläser and were washed with Acetone spectroscopic grade before use. Powder samples were sandwiched between two untreated glass plates.

Figure 2:
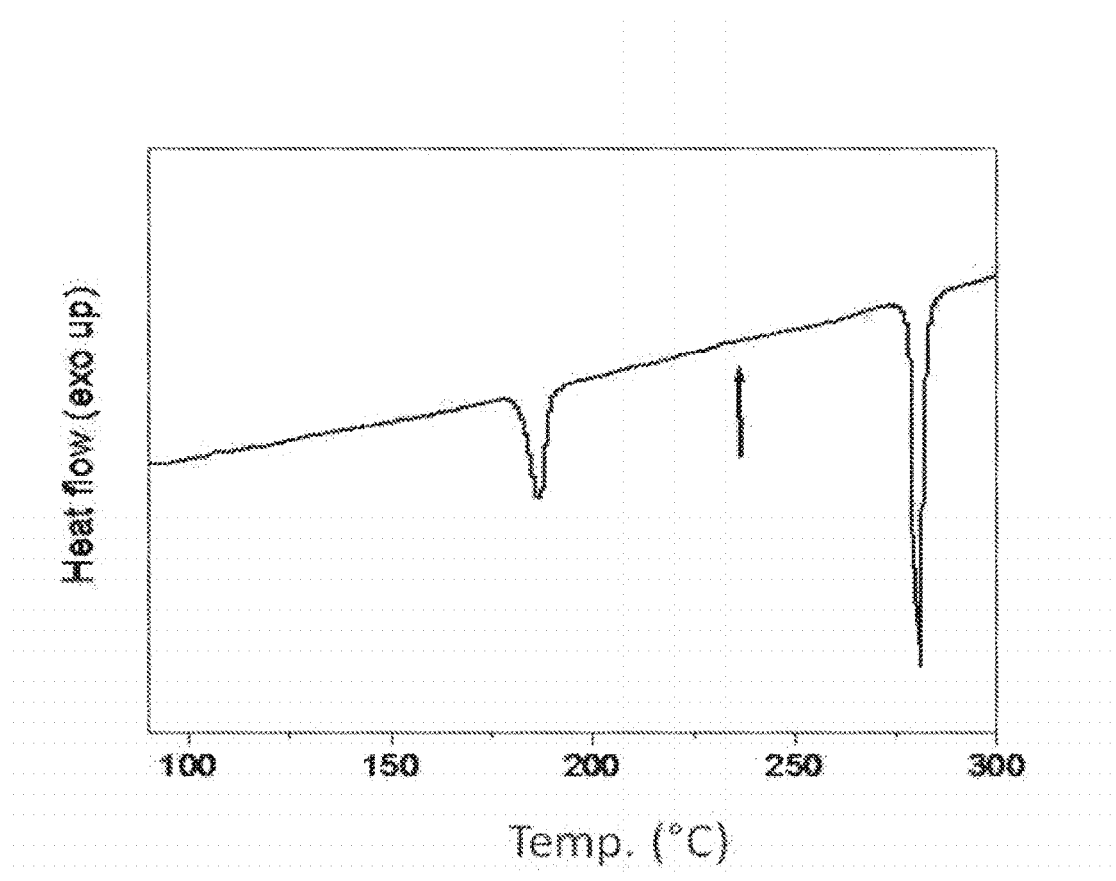
FIG. 2 is a DCS thermogram of a compound according to the present invention [2,2'-(2,2'-bithiophene-5,5'-diyl)bis(5-butyl-5H-thieno[2,3-c]pyrrole-4,6-dione)]

The DSC thermogram was recorded at 10° C./min under ambient conditions and is shown in FIG. 2. It shows a first endothermic peak at T=187° C. (10.2 J/g, second heating) and a second one corresponding to the melting, located at 280° C. (25.6 J/g). The cooling run (not shown here), showed a single transition corresponding to the crystallization located at 272° C. (−21.4 J/g).

Figure 3A:
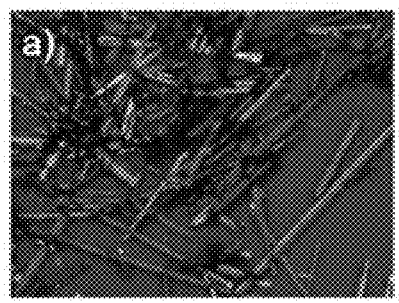
FIGS. 3A, 3B, 3C, 3D, 3E, and 3F show POM micrographs of a compound according to the present invention [2,2'-(2,2'-bithiophene-5,5'-diyl)bis(5-butyl-5H-thieno[2,3-c]pyrrole-4,6-dione)] in different phases.

POM analysis of 2,2'-(2,2'-bithiophene-5,5'-diyl)bis(5-butyl-5H-thieno[2,3-c]pyrrole-4,6-dione) is shown in FIGS. 3A-3F. In particular, FIG. 3A shows that the optical texture

TABLE 1

| Oligomer | λmax$^a$ [nm] | λPL$^{a,b}$ [nm] | E°$_{ox}$/ V vs. SCE | E°$_{red}$/ V vs. SCE | HOMO [eV] | LUMO [eV] |
|---|---|---|---|---|---|---|
| 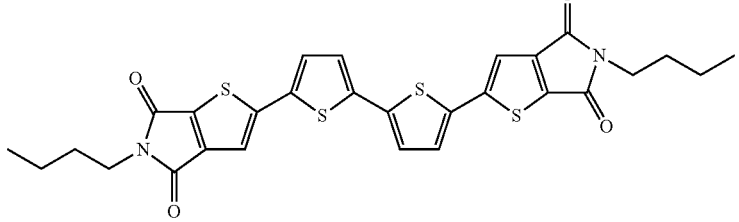 12 | 449 | 571 | 1.32 | −1.21$^c$ | −6.0$^d$ | −3.4$^d$ |
| 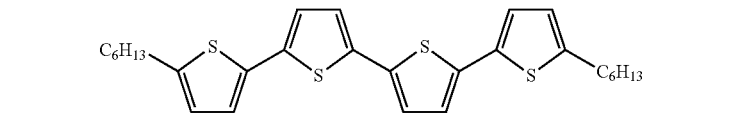 T4Hex | 401$^e$ | 463, 495, 527$^f$ | 0.98 | −2.17 | −5.5 | −2.4 |
| 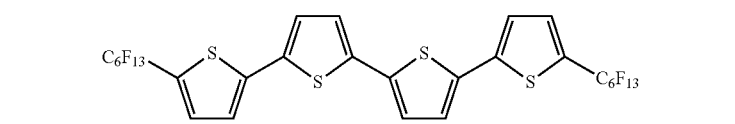 DFH-4T | 398$^g$ | 458, 489 | 1.35 | −1.53 | −6.2$^g$ | −3.3$^g$ |

$^a$in CH$_2$Cl$_2$,
$^b$λ$_{exc}$ = 449 nm,
$^c$vs SCE a 200 mV/sin CH$_2$Cl$_2$, 0.1 mol L$^{-1}$ (C$_4$H$_9$)$_4$NClO$_4$,
$^d$E$_{HOMO}$ = e (4.68 −E°$_{ox}$); E$_{LUMO}$ = e (4.68 −E°$_{red}$),
$^e$in toluene,
$^f$shoulder, from ref. Melucci et al, *Chem. Phys. Chem.* 2007, 8, 2621,
$^g$from A. Facchetti, M. Mushrush, H. E. Katz, T. J. Marks *Adv. Mat.* 15 (2003) 35-38.

Example 11: Registration of Thermal Properties

Figure 3B:
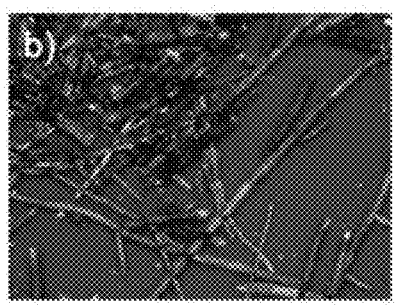
Figure 3C:
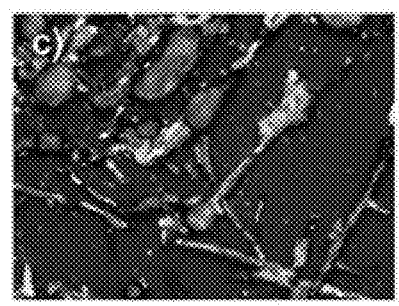
Figure 3D:
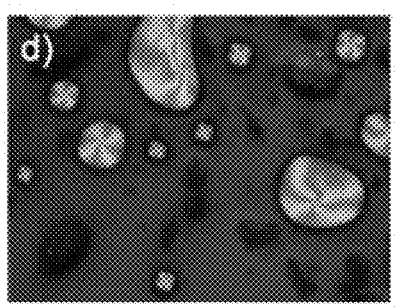
Figure 3E:
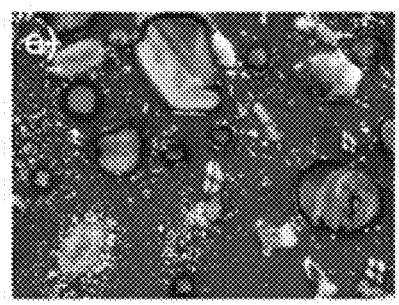
Figure 3F:
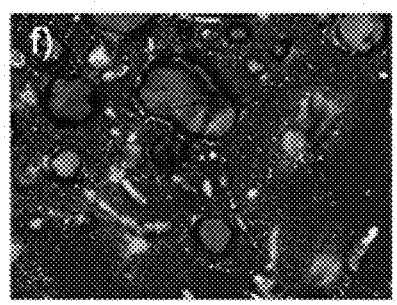

The thermal behavior of 2,2'-(2,2'-bithiophene-5,5'-diyl) bis(5-butyl-5H-thieno[2,3-c]pyrrole-4,6-dione) was investiof the compound in form of crystalline needles at RT; FIG. 3B shows transition to an LC phase between 198-280° C.; FIG. 3C shows mosaic texture at 280° C.; FIG. 3D shows nematic droplets between 290° C. and 295° C. before melting to isotropic phase; FIG. 3E shows crystalline domains growing from the melt; FIG. 3F shows crystalline phase at 260° C. on cooling to RT. The image of the micrographs is size 800 μm×800 μm.

Therefore, POM analysis of compound 12 according to the invention shows a marked increase in birefringence and fluidity in the range 198° C.-280° C. (FIG. 3B), but a mesophase texture can be seen immediately before the melting to isotropic liquid at 295° C. In fact, a mosaic texture (FIG. 3C) which evolves into nematic droplets (FIG. 3D) can be seen in the range 280-290° C. On cooling the melt, nucleation occurred at about 270° C. across the phase transition (FIG. 3E), and leads to crystalline domains that persist to room temperature (FIG. 3F). In thiophene oligomers melt-quenching have already proven to be a powerful method to enhance the molecular order of solution processed films and to promote charge transport in OFET.

Example 12: Registration of Single Crystal Structure

For single crystal analysis of 2,2'-(2,2'-bithiophene-5,5'-diyl)bis(5-butyl-5H-thieno[2,3-c]pyrrole-4,6-dione) (compound 12), the X-ray intensity data were measured on a Bruker SMART Apex II CCD area detector diffractometer. Cell dimensions and the orientation matrix were initially determined from a least-squares refinement on reflections measured in three sets of 20 exposures, collected in three different ω regions, and eventually refined against all data. For all crystals, a full sphere of reciprocal space was scanned by 0.3° ω steps. The software SMART was used for collecting frames of data, indexing reflections and determination of lattice parameters. The collected frames were then processed for integration by the SAINT program, and an empirical absorption correction was applied using SADABS. The structures were solved by direct methods (SIR 97) and subsequent Fourier syntheses and refined by full-matrix least-squares on $F^2$ (SHELXTL), using anisotropic thermal parameters for all non-hydrogen atoms. The hydrogen atoms bound to carbons were located in the Fourier maps, added in calculated positions, included in the final stage of refinement with isotropic thermal parameters, U(H)=1.2 Ueq(C) [U(H)=1.5 Ueq(C-Me)], and allowed to ride on their carrier atoms.

Figure 4A:
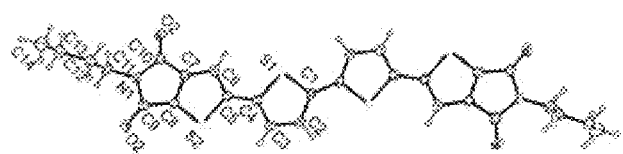
FIGS. 4A, 4B, and 4C show single crystal structure and molecular packing of a compound according to the present invention [2,2'-(2,2'-bithiophene-5,5'-diyl)bis(5-butyl-5H-thieno[2,3-c]pyrrole-4,6-dione)]
Figure 4B:
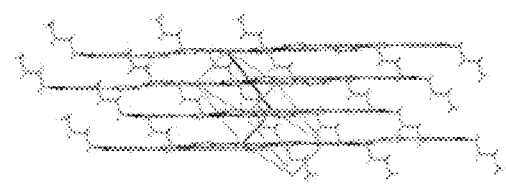
Figure 4C:
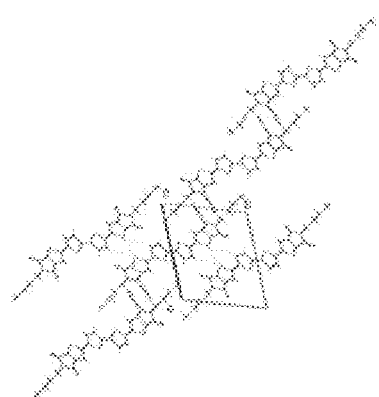

The molecular structure of 2,2'-(2,2'-bithiophene-5,5'-diyl)bis(5-butyl-5H-thieno[2,3-c]pyrrole-4,6-dione), (compound 12) shown in FIG. 4A illustrates that the molecule lies on a crystallographic inversion center located at the midpoint of the bond between the two thiophene units. The molecular backbone is almost planar being the two inner thiophene rings strictly coplanar and the dihedral angles between the thiophene and the thiophene-diimide units 4.4(5)°. In FIG. 4B and FIG. 4C, the crystal packing of compound 12 shows that the molecules adopt a slipped π-π stacking packing mode (interplanar distance ca. 3.51 Å, sliding along the long molecular axis 3.32 Å) instead of the herringbone structure more common for oligothiophenes. Moreover the molecules of adjacent π-π stacks are engaged in supramolecular 1D networks running across the bc plane formed through two intermolecular C—H . . . OH bonds (H11B . . . O1 2.54 Å, C11 . . . O1 3.48(1) Å, C11-H11B . . . O1 162°) in which two oxygen atoms in anti position (one for each fused ring) interact with one hydrogen atom of the carbon directly attached to the nitrogen of the diimide unit of two different molecules. This molecular arrangement is completed by intermolecular contacts involving the sulfur atoms of the fused thiophene diimide rings (S . . . S contacts 3.73 Å, sum of the sulfur van der Waals radii 3.7 Å) of neighbour molecules that do not participate to the C—H . . . O interactions. The same sulfur atoms are also engaged in weak C—H . . . S interactions (C—H . . . S, H . . . S 3.03 Å) with the inner hydrogens of the thiophene rings.

Example 13: Registration of Atomic Force Microscopy Images of Thin Films of 2,2'-(2,2'-bithiophene-5,5'-diyl)bis(5-butyl-5H-thieno[2,3-c]pyrrole-4,6-dione)

Semiconductor thin films were fabricated by solution cast as well as vacuum sublimation of 2,2'-(2,2'-bithiophene-5,5'-diyl)bis(5-butyl-5H-thieno[2,3-c]pyrrole-4,6-dione).

Figure 5A:
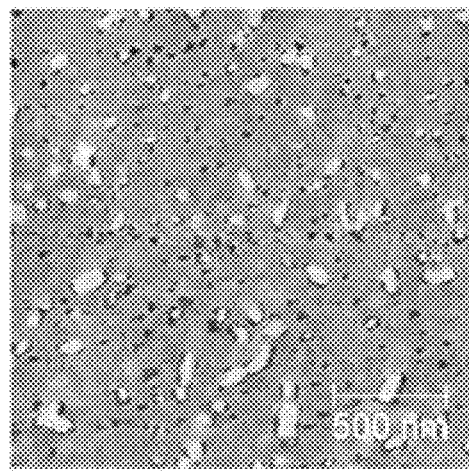
FIGS. 5A, 5B, and 5C show AFM images of films of different thicknesses of a compound according to the present invention [2,2'-(2,2'-bithiophene-5,5'-diyl)bis(5-butyl-5H-thieno[2,3-c]pyrrole-4,6-dione)]
Figure 5B:
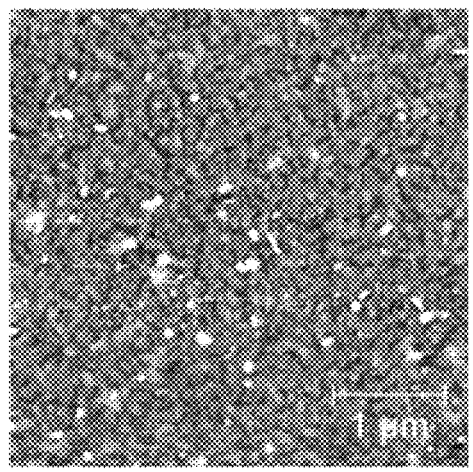
Figure 5C:
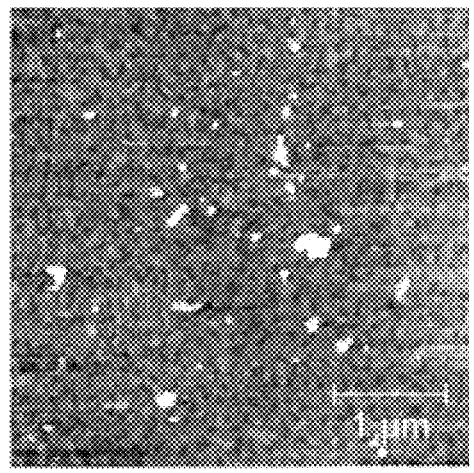

Thin films for surface morphology characterization has been grown by vacuum sublimation in a home-made vacuum chamber, with a deposition rate of 0.1 Å/s, at a base pressure of $10^{-6}$ mbar. The films were formed on glass/ITO/PMMA (450 nm) supports. In particular, three films of 2 nm, 10 nm and 20 nm respectively were formed and the film morphologies investigated by means a NT-MDT Solver Pro AFM atomic force microscope in tapping mode and X-ray diffraction. The obtained results are shown in FIGS. 5A, 5B, and 5C respectively. As shown in FIGS. 5A-5C, the films obtained by vacuum sublimation shows a layer by layer mechanism of growth, that is maintained also for high values of the film thickness, i.e. of 20 nm, see FIG. 5C. From the atomic force microscope (AFM) characterization, it may be concluded that the film surface morphology is highly bidimensional (RMS=3 nm) for all the film thicknesses relevant in FET devices applications. Such a flat and smooth film surface can guarantee a good organic/organic growth compatibility with a possible top layer and, for this reason, can be particularly suitable for the vertical heterojunction approach in realizing OLET structures.

Example 14: Registration of XRD Patterns of 2,2'-(2,2'-bithiophene-5,5'-diyl)bis(5-butyl-5H-thieno[2,3-c]pyrrole-4,6-dione)

X-ray diffraction (XRD) patterns of thin films and powder of 2,2'-(2,2'-bithiophene-5,5'-diyl)bis(5-butyl-5H-thieno[2,3-c]pyrrole-4,6-dione), (compound 12) were carried out by using a PANalytical X'PertPro diffractometer equipped with a fast solid state X'Celerator detector and a copper target (λ=0.15418 nm). Data were acquired in the 3-40° 2θ interval, by collecting 100 sec at each 0.05° step. In situ X-ray diffraction analysis of a thin film submitted to a temperature scan was also performed by using an Anton Paar TTK-450 sample stage. Few drops (≅200 μl) of a $CH_2Cl_2$ solution (2 mg/ml) of compound 12 were cast directly on the metallic sample holder at RT. After 1 h the temperature was increased at 10° C./min and the data collection was performed at fixed temperature (RT, 100°, 200°, 250°, 285° C.) counting 25 sec each 0.05° step in the range 3-8° 2θ in order to test the presence of the small angle reflections. Then the sample was cooled at 25° C./min. up to RT and then scanned again (100 sec/step).

Figure 6A:
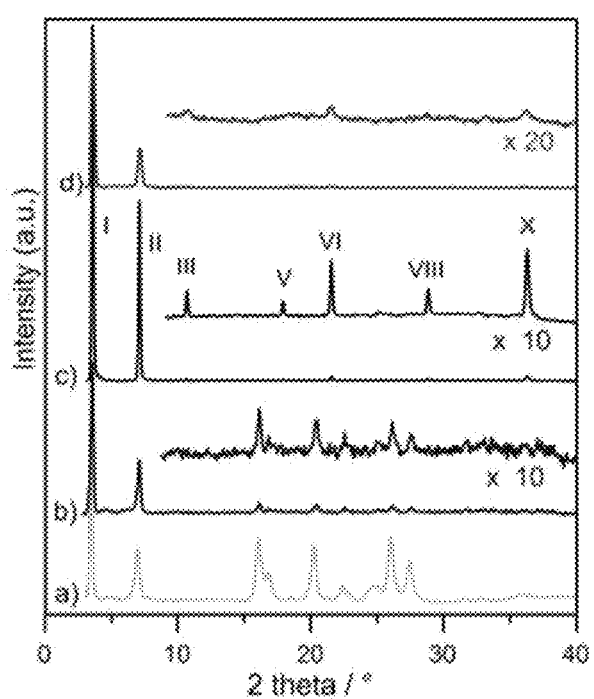
FIGS. 6A and 6B show XRD patterns of a compound according to the present invention [2,2'-(2,2'-bithiophene-5,5'-diyl)bis(5-butyl-5H-thieno[2,3-c]pyrrole-4,6-dione)] in different forms.

XRD patterns of a) a powder sample, b) a cast film (100 nm), c) cast-melt-quenched film (100 nm), d) a vacuum sublimed film (20 nm) of 2,2'-(2,2'-bithiophene-5,5'-diyl)bis(5-butyl-5H-thieno[2,3-c]pyrrole-4,6-dione) were recorded, and are displayed in FIG. 6A.

Figure 6B:
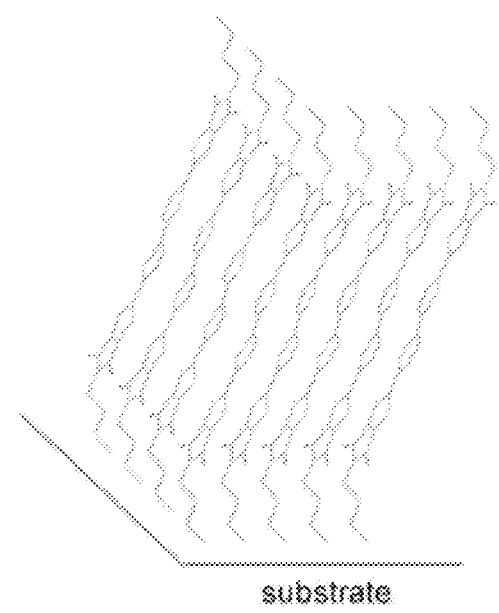

Several well resolved diffraction peaks are shown, confirming that an important degree of crystallinity has been obtained. The two peaks at 3.59 and 7.17° (2θ) are the most intense and correspond to the first and second order of a periodicity of 2.46 nm. Both are present either in powder or in film samples, suggesting they are directly connected with one important parameter of the structure. The film cast from a CH$_2$Cl$_2$ solution shows overall the same reflections of the powder sample, that means the presence of the same phase and a random orientation of the crystal domains in the film. After the film melting at 285° C. and rapid cooling at RT, the XRD pattern of the film changes completely. At a glance only the two peaks in the small angle region are appreciable, but at high magnification others reflections due to higher order periodicity of the 24.6 nm distance, up to the 10th, are found. Being the molecular length about 2.8 nm and the projection on its main plane is 2.6 nm, the period of 2.46 nm, measured from the XRD pattern of film samples, suggests an arrangement of the molecules close to a vertical position respect to the substrate as roughly sketched in FIG. 6B. Crystal data and structure refinement of 2,2'-(2,2'-bithiophene-5,5'-diyl)bis(5-butyl-5H-thieno[2,3-c]pyrrole-4,6-dione) (compound 12) are summarized as follows:

| Compound | 12 |
| --- | --- |
| Formula | C$_{28}$H$_{24}$N$_2$O$_4$S$_4$ |
| M | 580.73 |
| T, K | 293 (2) |
| Crystal symmetry: | Triclinic |
| Space group | P-1 |
| a, Å | 4.841 (4) |
| b, Å | 11.278 (7) |
| c, Å | 12.907 (9) |
| α, ° | 71.880 (9) |
| β, ° | 86.80 (1) |
| γ, ° | 86.93 (1) |
| V, Å$^3$ | 668.2 (8) |
| Z | 1 |
| Dc, Mg m$^{-3}$ | 1.443 |
| μ (Mo—K$_\alpha$), mm$^{-1}$ | 0.394 |
| F(000) | 302 |
| Crystal size, mm | 0.50 × 0.02 × 0.01 |
| θ limits, ° | 1.66-24.00 |
| Reflections collected | 5269 |
| Unique obs. reflections [Fo > 4σ(Fo)] | 2053 |
| Goodness-of-fit-on F$^2$ | 0.937 |
| R$_1$ (F)a [Fo > 4σ (Fo)] | 0.0956 |
| wR$_2$ (F$^2$)$^b$ | 0.2337 |
| Largest diff. peak and hole, e.Å-3 | −0.448 and 1.228 |

Example 15: Fabrication of an Organic Thin Film Transistor

An organic thin film transistor (OTFT) was fabricated in bottom gate-top contact geometry. The ITO substrate cleaning procedure used consist of two sonication cycles, in acetone first and 2-isopropanol then, for 10 minutes each. The 450 nm thick dielectric layer of PMMA has been grown by spin-coating on top of the clean ITO substrate (relative electric permittivity ∈=3.6 at 100 Hz). The PMMA film was then thermally annealed in a glove box at 120° C. (around 10° C. above the glass transition temperature for PMMA) for 15 hours under inert atmosphere. The 30 nm thick layer of 2,2'-(2,2'-bithiophene-5,5'-diyl)bis(5-butyl-5H-thieno[2,3-c]pyrrole-4,6-dione) has been grown by vacuum sublimation in a home-made vacuum chamber, with a deposition rate of 0.1 Å/s, at a base pressure of 10$^{-6}$ mbar. Gold source-drain contacts are then deposited on top of the organic film, properly masked to form a 70 μm length and a 15 mm width channel. The substrate temperature during the film deposition has been kept at room temperature (RT).

The electrical measurements are performed by means of a Suss PM5 professional probe station connected with an Agilent B1500A parametric analyzer located inside a dry inert glove box. The probe station has been equipped with a Hamamatsu S1337 photodiode with an active area of 1 cm$^2$, located under the OTFT channel, in order to collect the electroluminescence originating from the working device. Further device features were:

$C_{PMMA}$=7.08 nF/cm$^2$

The electrical response of the fabricated OTFT has been measured in nitrogen controlled atmosphere, using a commercial probe station Suss PM5 professional probe station equipped with a photodiode in order to collect possible electroluminescence originating from the working device. The probe station is integrated with a B1500 Agilent parametric analyzer. The obtained results consist in the graphs reported in FIGS. 7A-7E.

Figure 7A:
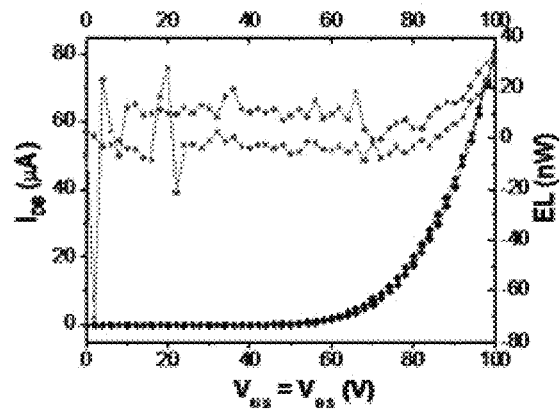
FIGS. 7A, 7B, 7C, 7D, and 7E show graphs reporting the optoelectronic features of an OTFT comprising a compound according to the present invention [2,2'-(2,2'-bithiophene-5,5'-diyl)bis(5-butyl-5H-thieno[2,3-c]pyrrole-4,6-dione)] as semiconductor layer.
Figure 7B:
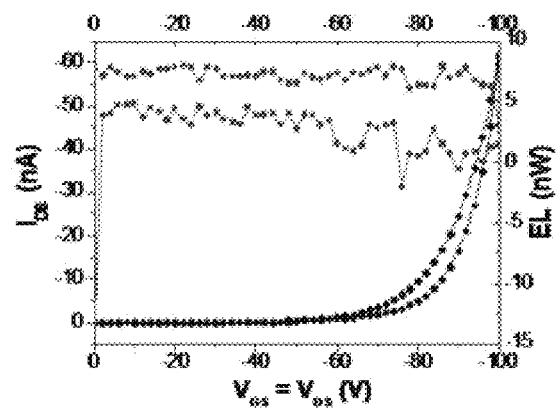
Figure 7C:
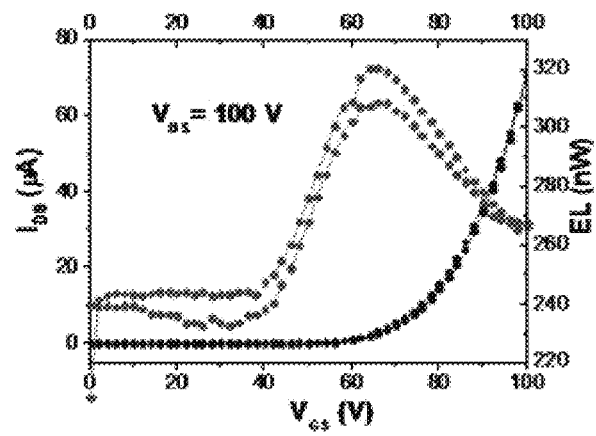
Figure 7D:
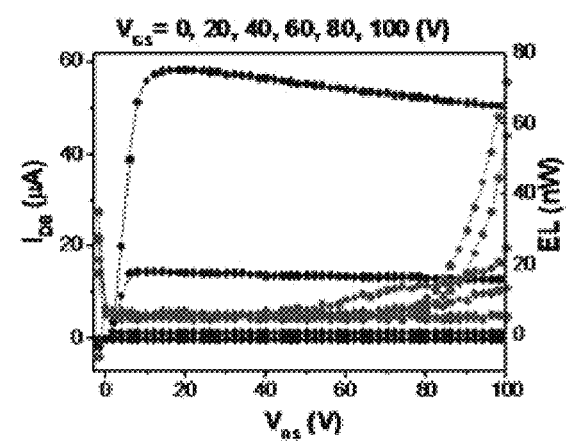
Figure 7E:
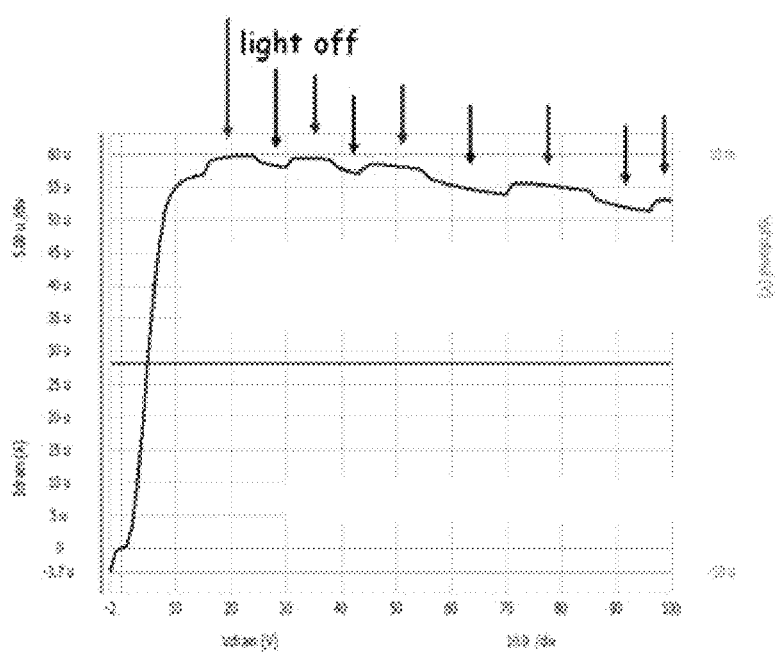

Electrical characterization of the realized OTFT shows ambipolar behavior. The electron contribution is the most relevant as the high value (0.053 cm$^2$/Vs, $V_T^N$=60 V) of the N-type mobility demonstrates, as it can be seen in FIG. 7A showing locus curve N type. A three-order-of-magnitude lower hole mobility ($\mu_P$=6.4×10$^{-5}$ cm$^2$/V×s, $V_T^P$=−71 V) has been calculated from the P-type locus curve reported in FIG. 7B. In spite of the low value of the hole current contribution, this feature plays a major role in the generation of the electroluminescence signal clearly visible in the Transfer saturation N-type and multiple output N-type curves reported in FIGS. 7C and 7D, respectively. The light emission signal of the Transfer curve is peaked in the ambipolar working region of the device, in agreement with the typical behavior reported for single layer ambipolar Organic Light Emitting Transistors (OLET). Moreover, correlated to the presence of environmental light, an increase of the total OTFT flowing current has been detected. In FIG. 7E is reported a single output curve collected by switching the measurement condition from the complete dark, to the presence of a neon lamp. Each step, recognizable in the saturation portion of the curve, is correlated to the light-on measurement condition. This behavior can be described in terms of photocurrent generation. In conclusion, the results obtained from the opto-electronic characterization of single layer OTFTs based on 2,2'-(2,2'-bithiophene-5,5'-diyl)bis(5-butyl-5H-thieno[2,3-c]pyrrole-4,6-dione), make this compound suitable not only for charge transport application in Field Effect configuration, but also for light emitting supplications (OLETs) as well as for light sensing (Light Sensing Field Effect Transistors) or organic photovoltaic applications.

The invention claimed is:

1. A compound having formula selected in the group consisting of formula (I), formula (II), formula (III) and formula (IV):

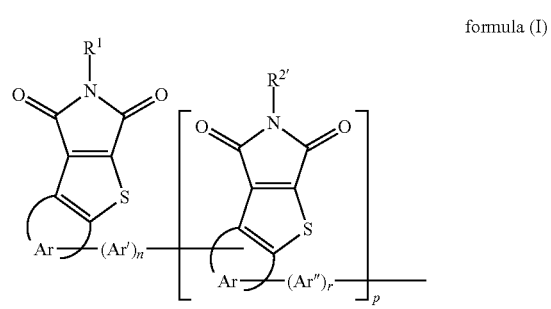

formula (I)

formula (II)

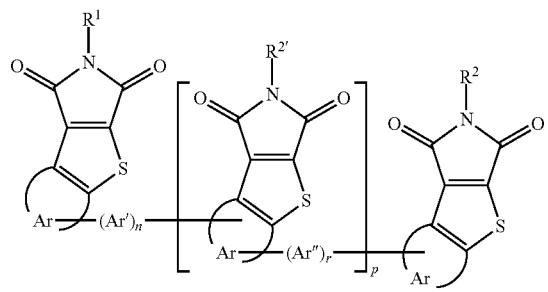

formula (III)

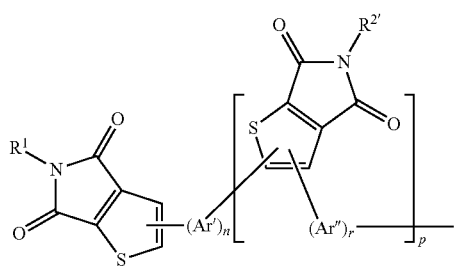

formula (IV)

wherein:
- R¹, R² and R²' independently of each other, are selected in the group consisting of hydrogen, $C_1$-$C_{40}$ linear or branched alkyl groups, $C_1$-$C_{40}$ linear or branched heteroalkyl groups, $C_3$-$C_{40}$ linear or branched cycloalkyl groups, $C_1$-$C_{40}$ linear or branched hydroxyalkyl groups, $C_1$-$C_{40}$ linear or branched alkoxyl groups, $C_1$-$C_{40}$ linear or branched alkylcarboxylic groups, $C_1$-$C_{40}$ linear or branched alkylcarboxamide groups, $C_1$-$C_{40}$ linear or branched alkylsulphonic groups, and $C_1$-$C_{40}$ linear or branched nitrile groups;
- Ar is selected in the group consisting of monocyclic aryl groups, polycyclic aryl groups, monocyclic heteroaryl groups and polycyclic heteroaryl groups;
- Ar' and Ar", independently of each other, are selected in the group consisting of monocyclic aryl groups, polycyclic aryl groups, monocyclic heteroaryl groups and polycyclic heteroaryl groups;
- n and r, independently of each other, are integers between 1 and 50; and
- p is an integer between 0 and 5;

with the exception of compounds of formula A:

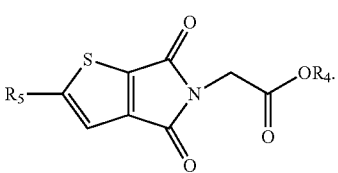

formula A wherein $R_4$ is selected in the group consisting of $C_1$-$C_4$ alkyls; and $R_5$ is selected in the group consisting of monocyclic aryl groups and substituted monocyclic aryl groups;

and with the exception of compounds of formula B:

formula B wherein $R_6$ is selected in the group consisting of isopropyl, cyclopropyl and terbutyl groups and $R_7$ is selected in the group consisting of phenyl, 2-fluorphenyl, 3-fluorphenyl, 4-fluorphenyl, 2-chlorphenyl, 3-chlorphenyl, 4-chlorphenyl, 2-methylphenyl, 3-methylphenyl, 4-methylphenyl, 2-trifluoromethylphenyl, 3-trifluormethylphenyl, 4-trifluormethylphenyl, 2-methoxyphenyl, 3-methoxyphenyl, 4-methoxyphenyl, 2,4-dichlorphenyl, 2,4,6-trimethylphenyl, 2-thienyl, 3-thienyl, 2-pyridyl, 3-pyridyl, 4-pyridyl.

2. The compound according to claim 1, wherein when p is 0, n is between 2 and 50.

3. The compound according to claim 1, having formula selected in the group consisting of formula (Ia), formula (IIa), formula (IIIa) and formula (IVa)

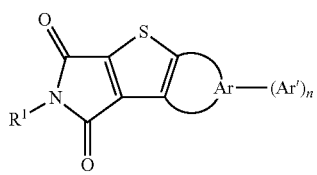

formula (Ia)

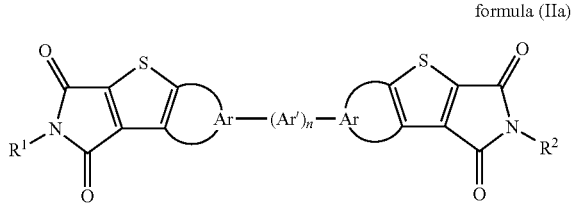

formula (IIa)

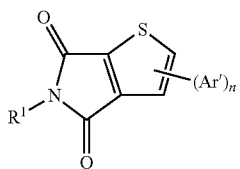

formula (IIIa)

formula (IVa)

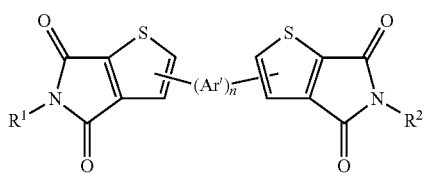

wherein:
R¹ and R², independently of each other, are selected in the group consisting of hydrogen, $C_1$-$C_{40}$ linear or branched alkyl groups, $C_1$-$C_{40}$ linear or branched heteroalkyl groups, $C_3$-$C_{40}$ linear or branched cycloalkyl groups, $C_1$-$C_{40}$ linear or branched hydroxyalkyl groups, $C_1$-$C_{40}$ linear or branched alkoxyl groups, $C_1$-$C_{40}$ linear or branched alkylcarboxylic groups, $C_1$-$C_{40}$ linear or branched alkylcarboxyamide groups, $C_1$-$C_{40}$ linear or branched alkylsulphonic groups, and $C_1$-$C_{40}$ linear or branched nitrile groups;

Ar is selected in the group consisting of monocyclic aryl groups, polycyclic aryl groups, monocyclic heteroaryl group and polycyclic heteroaryl group;

Ar' is a moiety selected in the group consisting of a monocyclic aryl group, polycyclic aryl group, monocyclic heteroaryl group and polycyclic heteroaryl group.

4. The compound according to claim 3, wherein Ar is selected in the group consisting of the following rings (f), (g), (h), (i), (l), (m), (n), (o), (p):

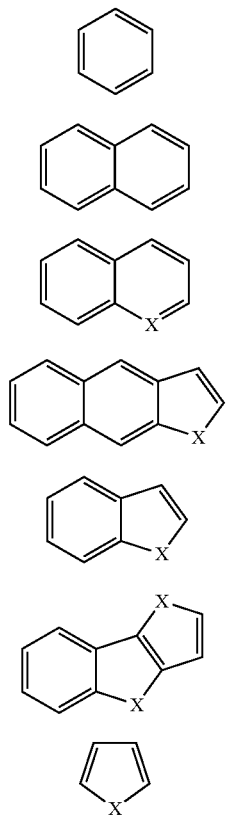

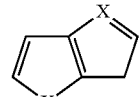

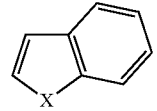

wherein X is selected in the group consisting of S, O, Si, Se, NR³,
R³ being selected in the group consisting of $C_1$-$C_{12}$ linear or branched alkyl groups, $C_1$-$C_{12}$ linear or branched halogenoalkyl groups, $C_3$-$C_{12}$ linear or branched cycloalkyl groups, $C_1$-$C_{12}$ linear or branched hydroxyalkyl groups, $C_1$-$C_{12}$ linear or branched alkoxyl groups, $C_1$-$C_{12}$ linear or branched alkylcarboxylic groups, $C_1$-$C_{12}$ linear or branched alkylcarboxyamide groups, $C_1$-$C_{12}$ linear or branched alkylsulphonic groups, and $C_1$-$C_{12}$ linear or branched nitrile groups.

5. The compound according to claim 1, wherein R¹, R², independently of each other, are selected in the group consisting of $C_1$-$C_{12}$ linear or branched alkyl groups, $C_1$-$C_{12}$ linear or branched heteroalkyl groups, $C_3$-$C_{12}$ linear or branched cycloalkyl groups, $C_1$-$C_{12}$ linear or branched hydroxyalkyl groups, $C_1$-$C_{12}$ linear or branched alkoxyl groups, $C_1$-$C_{12}$ linear or branched alkylcarboxylic groups, $C_1$-$C_{12}$ linear or branched alkylcarboxyamide groups, $C_1$-$C_{12}$ linear or branched alkylsulphonic groups, and $C_1$-$C_{12}$ linear or branched nitrile groups.

6. The compound according to claim 1, wherein Ar' is a unit selected in the group consisting of the following units (a), (b), (c):

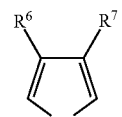

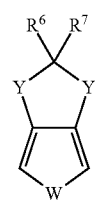

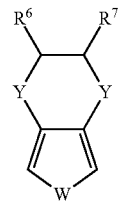

wherein W is selected in the group consisting of S, SO and $SO_2$;
Y is selected in the group consisting of S, O and NR⁸; and
R⁶, R⁷, and R⁸ independently of each other, are selected in the group consisting of hydrogen, $C_1$-$C_{12}$ linear or branched alkyl groups, $C_1$-$C_{12}$ linear or branched halogenoalkyl groups, $C_3$-$C_{12}$ linear or branched cycloalkyl groups, $C_1$-$C_{12}$ linear or branched hydroxyalkyl groups, $C_1$-$C_{12}$ linear or branched alkoxyl groups, $C_1$-$C_{12}$ linear or branched alkylcarboxylic groups, $C_1$-$C_{12}$ linear or branched alkylcarboxyamide groups, $C_1$-$C_{12}$ linear or branched alkylsulphonic groups, and $C_1$-$C_{12}$ linear or branched nitrile groups.

7. The compound according to claim 1 having the following formula (V):

formula (V)

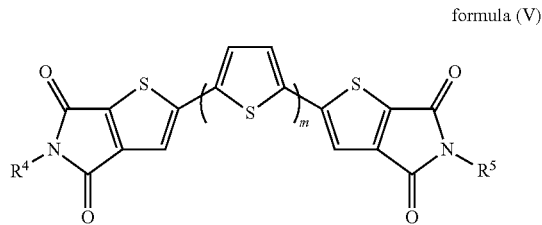

wherein $R^4$ and $R^5$, independently of each other, are selected in the group consisting of $C_1$-$C_8$ linear or branched saturated alkyl groups, $C_1$-$C_8$ linear or branched fluoroalkyl groups, $C_1$-$C_8$ linear or branched heteroalkyl groups comprising a heteroatom selected among O, S, N; and m is an integer between 1 and 30.

8. The compound according to claim 7, having formula (VI):

formula (VI)

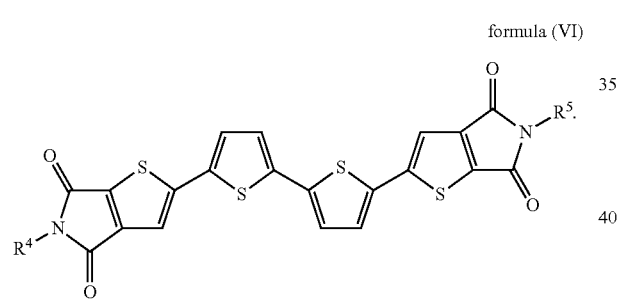

9. The compound according to claim 1, having the following formula (VII):

formula (VII)

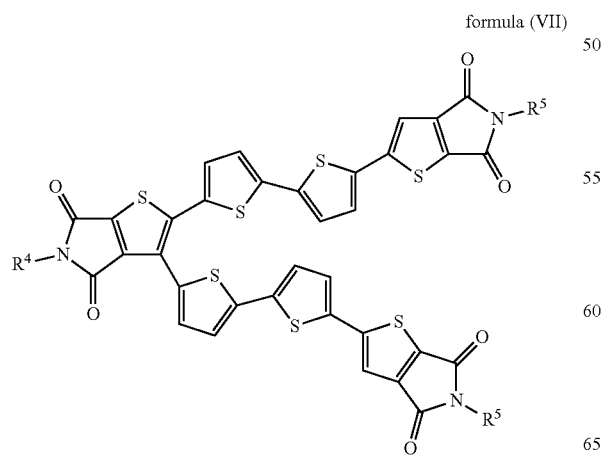

wherein $R^4$ and $R^5$, independently of each other, are selected in the group consisting of $C_1$-$C_8$ linear or branched saturated alkyl groups, $C_1$-$C_8$ linear or branched fluoroalkyl groups, $C_1$-$C_8$ linear or branched heteroalkyl groups comprising a heteroatom selected among O, S, N.

10. An electronic device comprising:
a compound having formula selected in the group consisting of formula (I), formula (II), formula (III) and formula (IV):

formula (I)

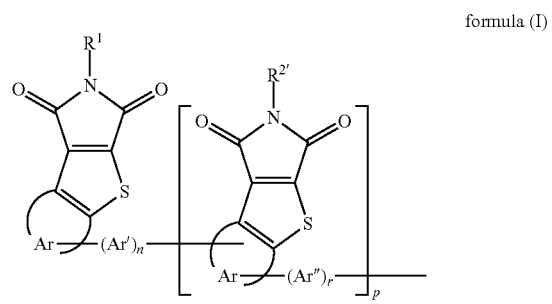

formula (II)

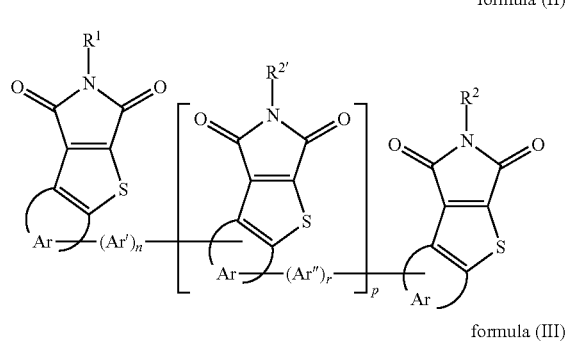

formula (III)

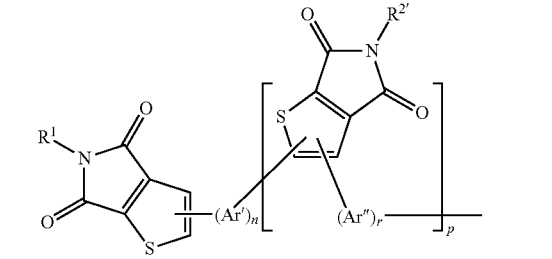

formula (IV)

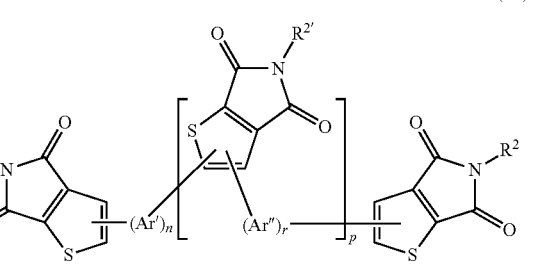

wherein:
$R^1$, $R^2$ and $R^{2'}$ independently of each other, are selected in the group consisting of hydrogen, $C_1$-$C_{40}$ linear or branched alkyl groups, $C_1$-$C_{40}$ linear or branched heteroalkyl groups, $C_3$-$C_{40}$ linear or branched cycloalkyl groups, $C_1$-$C_{40}$ linear or branched hydroxyalkyl groups, $C_1$-$C_{40}$ linear or branched alkoxyl groups, $C_1$-$C_{40}$ linear or branched alkylcarboxylic groups, $C_1$-$C_{40}$ linear or branched alkylcarboxyamide groups, $C_1$-$C_{40}$ linear or branched alkylsulphonic groups, and $C_1$-$C_{40}$ linear or branched nitrile groups;

Ar is selected in the group consisting of monocyclic aryl groups, polycyclic aryl groups, monocyclic heteroaryl groups and polycyclic heteroaryl groups;

Ar' and Ar", independently of each other, are selected in the group consisting of monocyclic aryl groups, polycyclic aryl groups, monocyclic heteroaryl groups and polycyclic heteroaryl groups;

n and r, independently of each other, are integers between 1 and 50; and p is an integer between 0 and 5;

as an organic semiconductor material.

11. An electronic device comprising:
the compound according to claim 2 as an organic semiconductor material.

12. The electronic device according to claim 10, wherein the organic semiconductor material is an n-type organic semiconductor material.

13. An electronic device comprising a semiconductor layer in contact with a number of electrodes, wherein the semiconductor layer includes at least one compound having formula selected in the group consisting of formula (I), formula (II), formula (III) and formula (IV):

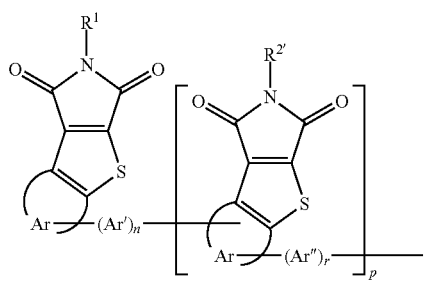

formula (I)

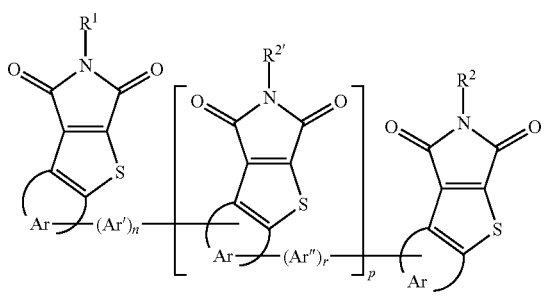

formula (II)

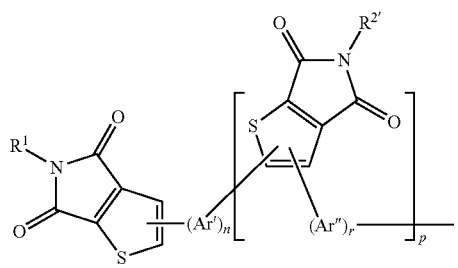

formula (III)

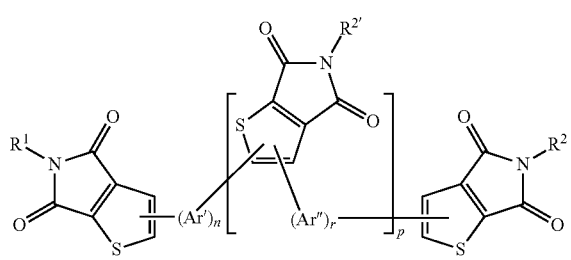

formula (IV)

wherein:

$R^1$, $R^2$ and $R^{2'}$ independently of each other, are selected in the group consisting of hydrogen, $C_1$-$C_{40}$ linear or branched alkyl groups, $C_1$-$C_{40}$ linear or branched heteroalkyl groups, $C_3$-$C_{40}$ linear or branched cycloalkyl groups, $C_1$-$C_{40}$ linear or branched hydroxyalkyl groups, $C_1$-$C_{40}$ linear or branched alkoxyl groups, $C_1$-$C_{40}$ linear or branched alkylcarboxylic groups, $C_1$-$C_{40}$ linear or branched alkylcarboxyamide groups, $C_1$-$C_{40}$ linear or branched alkylsulphonic groups, and $C_1$-$C_{40}$ linear or branched nitrile groups;

Ar is selected in the group consisting of monocyclic aryl groups, polycyclic aryl groups, monocyclic heteroaryl groups and polycyclic heteroaryl groups;

Ar' and Ar", independently of each other, are selected in the group consisting of monocyclic aryl groups, polycyclic aryl groups, monocyclic heteroaryl groups and polycyclic heteroaryl groups;

n and r, independently of each other, are integers between 1 and 50; and p is an integer between 0 and 5.

14. An electronic device comprising a semiconductor layer in contact with a number of electrodes, wherein the semiconductor layer includes at least one compound according to claim 2.

* * * * *